(12) United States Patent
Shekhawat et al.

(10) Patent No.: US 7,759,924 B2
(45) Date of Patent: Jul. 20, 2010

(54) CASCADED MOSFET EMBEDDED MULTI-INPUT MICROCANTILEVER

(75) Inventors: Gajendra Shekhawat, Arlington Heights, IL (US); Vinayak P Dravid, Glenview, IL (US); Soo-Hyun Tark, Evanston, IL (US); Arvind K Srivastava, Des Plaines, IL (US)

(73) Assignee: Northwestern University, Evanston, IL (US)

( * ) Notice: Subject to any disclaimer, the term of this patent is extended or adjusted under 35 U.S.C. 154(b) by 380 days.

(21) Appl. No.: 11/566,557

(22) Filed: Dec. 4, 2006

(65) Prior Publication Data

US 2007/0145966 A1 Jun. 28, 2007

Related U.S. Application Data

(63) Continuation-in-part of application No. 10/996,274, filed on Nov. 23, 2004, now Pat. No. 7,157,897.

(60) Provisional application No. 60/524,994, filed on Nov. 25, 2003.

(51) Int. Cl.
   *G01N 27/00* (2006.01)
   *G01B 5/28* (2006.01)

(52) U.S. Cl. .................... 324/71.1; 73/105; 73/580

(58) Field of Classification Search ............ 73/580
    See application file for complete search history.

(56) References Cited

U.S. PATENT DOCUMENTS

| | | | |
|---|---|---|---|
| 5,458,222 A | 10/1995 | Pla et al. | |
| 5,742,377 A | 4/1998 | Minne et al. | |
| 5,930,666 A | 7/1999 | Pankove | |
| 5,953,603 A | 9/1999 | Kim | |
| 5,989,968 A * | 11/1999 | Kim et al. | 438/365 |
| 6,066,265 A * | 5/2000 | Galvin et al. | 216/2 |
| 6,203,983 B1 | 3/2001 | Quate et al. | |
| 6,237,399 B1 * | 5/2001 | Shivaram et al. | 73/105 |
| 6,613,601 B1 | 9/2003 | Krauss et al. | |
| 6,680,788 B1 | 1/2004 | Roberson et al. | |
| 6,713,389 B2 | 3/2004 | Speakman | |
| 6,777,529 B2 | 8/2004 | Ong et al. | |
| 6,906,450 B2 | 6/2005 | De Miguel et al. | |
| 2002/0070737 A1 * | 6/2002 | Gilton | 324/718 |
| 2008/0272306 A1 * | 11/2008 | Greywall | 250/385.1 |

OTHER PUBLICATIONS

G. Miller, W.C. Inkret, M.E. Schillaci, H.F. Martz, T.T. Little. Health Physics. vol. 78 (2000) 598.

N. Iznaga, G. Nunez, J. Solozabal, A. Morales, E. Artaza, R. Rubio, E. Cardenas, Computer Methods and Programs in Biomedicine, vol. 47 (1995) 1678.

(Continued)

*Primary Examiner*—Timothy J Dole
*Assistant Examiner*—John Zhu
(74) *Attorney, Agent, or Firm*—McAndrews, Held & Malloy, Ltd.

(57) ABSTRACT

A sensor for detecting mechanical perturbations represented by a change in an electrical signal includes a structure such as a cantilever, membrane, etc. and a field effect transistor such as a MOSFET embedded in the structure. The drain current of the embedded transistor changes with mechanical perturbations in the structure caused, for example, by a biochemical interaction being sensed. A scanning probe microscope utilizes the embedded MOSFET with a BiMOS actuator.

22 Claims, 37 Drawing Sheets

OTHER PUBLICATIONS

W. Gopel, Chemical imaging. I. Concepts and visions for electronic and bioelectronics noises, sensors and actuators B, B52 (1998) 125.

C. Nicollnl, Thin solid films, vol. 284-285 (1996) 1; O.H. Willemsen, M.M.E. Snel, A. Cambi, J. Greve, B.G. Gooth, C.G. Figdor, Biophysical Journal, vol. 79 (2000) 3276.

M. Gomez-Lopez, J.A. Preece, J.F. Stoddart, Nanotechnology, vol. 7 1996 183.

M. Bras, J. Cloarec, F. Bessueille, E. Souteyrand. J. Martin, Journ. of Fluores., vol. 10 (2000) 247.

J. Fritz, M.K. Bailer, H.P. Lang, H. Rothuizen, P. Vettiger, E. Meyer, H.J. Guntherodt, Ch. Gerber, J.K. Gimzewski, Translating biomolecular recognition into nanomechanics, Science 288: 316-318 (2000).

R. McKendry, J.Y. Zhang, Y. Arntz, T. Strunz, M. Hegner, H.P. Lang, M.K. Bailer, U. Certa, E. Meyer, H.J. GuntherodL C. Gerber, Multiple label-free biodetection and quantitive DNA-binding assa s on a nanomechanical cantilever array, PNAS 99: 9783-9788 (2002).

Y. Arntz, J.D. Seelig, H.P. Lang, J. Zhang, P. Hunziker, J.P. Ramseyer, E. Meyer, M. Hegner, C. Gerber, Label-free protein assay based on a nanomechanical cantilever array, Nanotechnology 14: 86-90 (2003).

R. Berger, E. Delmarche, H.P. Lang, Ch. Gerber, J.K. Gimzewski, E. Meyer, H.J. Guntherodt, Surface stress I the self assembly of alkanethiols on gold, Science, vol. 276 (1997) 2021.

S.J. O'Shea, M.E. Welland, TA Brunt, A. Ramadan, T. Rayment, Atomic force microscopy stress sensors for studies in liquids, J. Vac. Si. Technol., vol. B14 (1996) 1383.

M. Tortonese, R.C. Barrett, C.F. Quate, Atomic resolution with an atomic force microscope using piezoresistive detection, Appl. Phys. Letters, vol. 62 (1993) 834.

A. Boisen, J. Thaysen, H. Jensenius and O. Hansen, Environmental sensors based on micromachined cantilevers with Integrated readout, Ultramicroscopy 82 (2000) 11-16.

S. Minne, G. Yaralioglu, S. Manalis, JA Adams, C. Quate, Appl. Phys. Lett., vol. 72 (1998) 2340.

S.C. Minne, S.R. Manalis, C.F. Quate, Integrated piezo-resistive and piezo-actuator based parallel scanning probe microscope, Appl. Phys. Letts., vol. 67 (1995) 3918.

IBM Creates World's Highest Performing Nanotube Transistors, IBM Press Release (May 20, 2002).

International Search Resort for Application No. PCT/US2004/39685 (Nov. 16, 2005).

IBM Press Release, http://dominosesearchibm.com/comm/pr.nsf/pages/news.20020520_nanotubes.html, May 20, 2002.

* cited by examiner

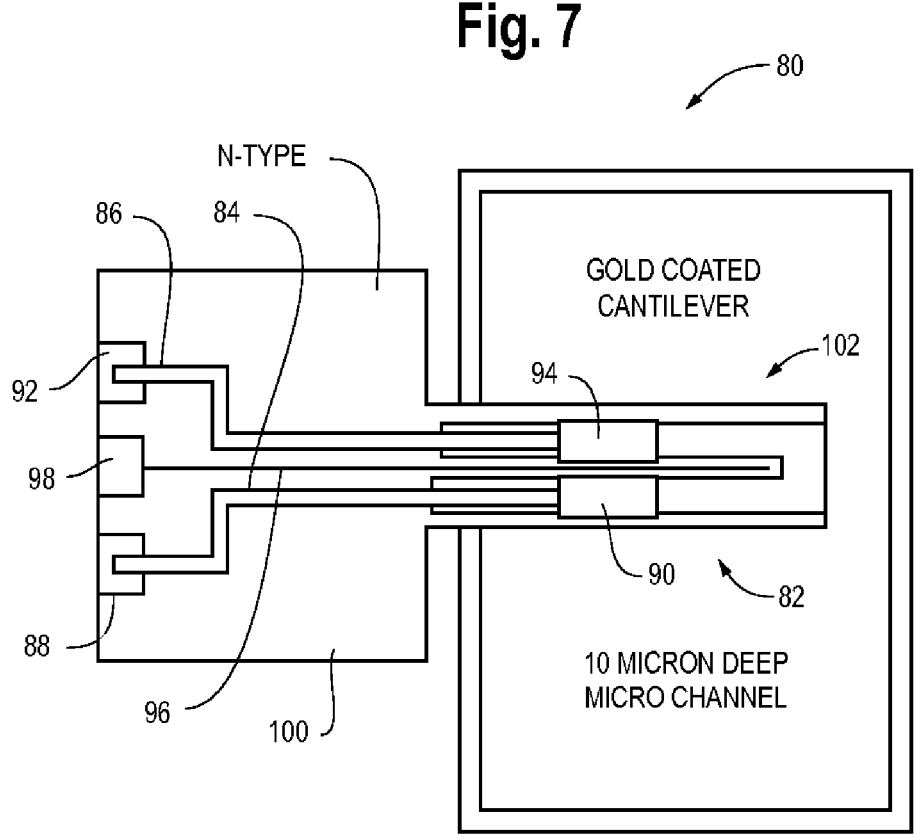

⇧ CHANGE IN DRAIN CURRENT VS. DRAIN VOLTAGE AT Gv = 1.0 V FOR 40 nM TARGET ssDNA.

⇧ DRAIN CURRENT VS. TIME FOR 40 nM TARGET ssDNA HYBRIDIZATION AT Gv = 1.0 V AND Dv = 6.0 V. DRAIN CURRENT DECEASED WITH HYBRIDIZATION TIME AND REACHED SATURATION IN ~30 MIN.

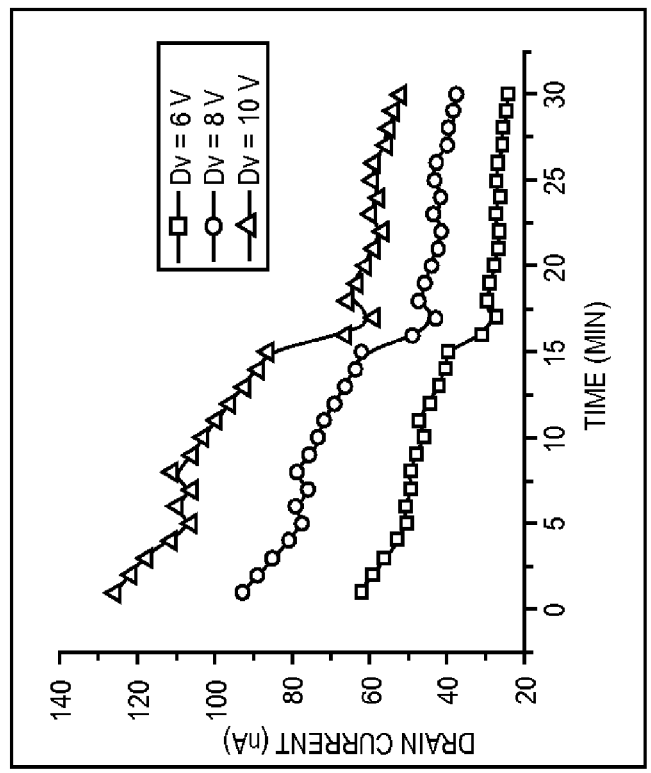
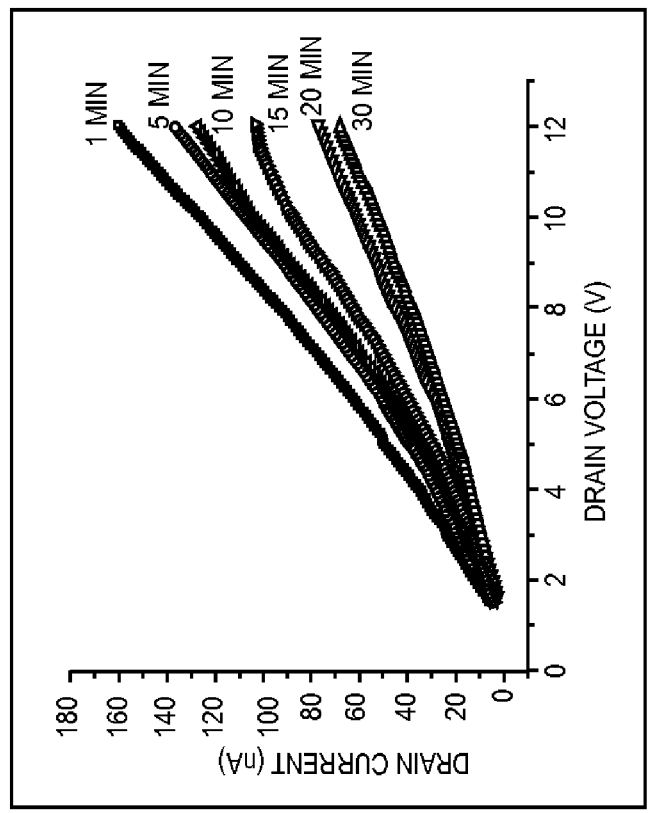

DRAIN CURRENT VS. TIME FOR 3 DIFFERENT DRAIN VOLTAGES.

DRAIN CURRENT VS. DRAIN VOLTAGE AT Gv = 1.0 V. DRAIN CURRENT DECREASED WITH ANTIGEN (0.1 mg/ml) ANTIBODY (0.1 mg/ml) BINDING

Fig. 25
CASCADED MOSFET EMBEDDED MULTI-INPUT MICROCANTILEVER
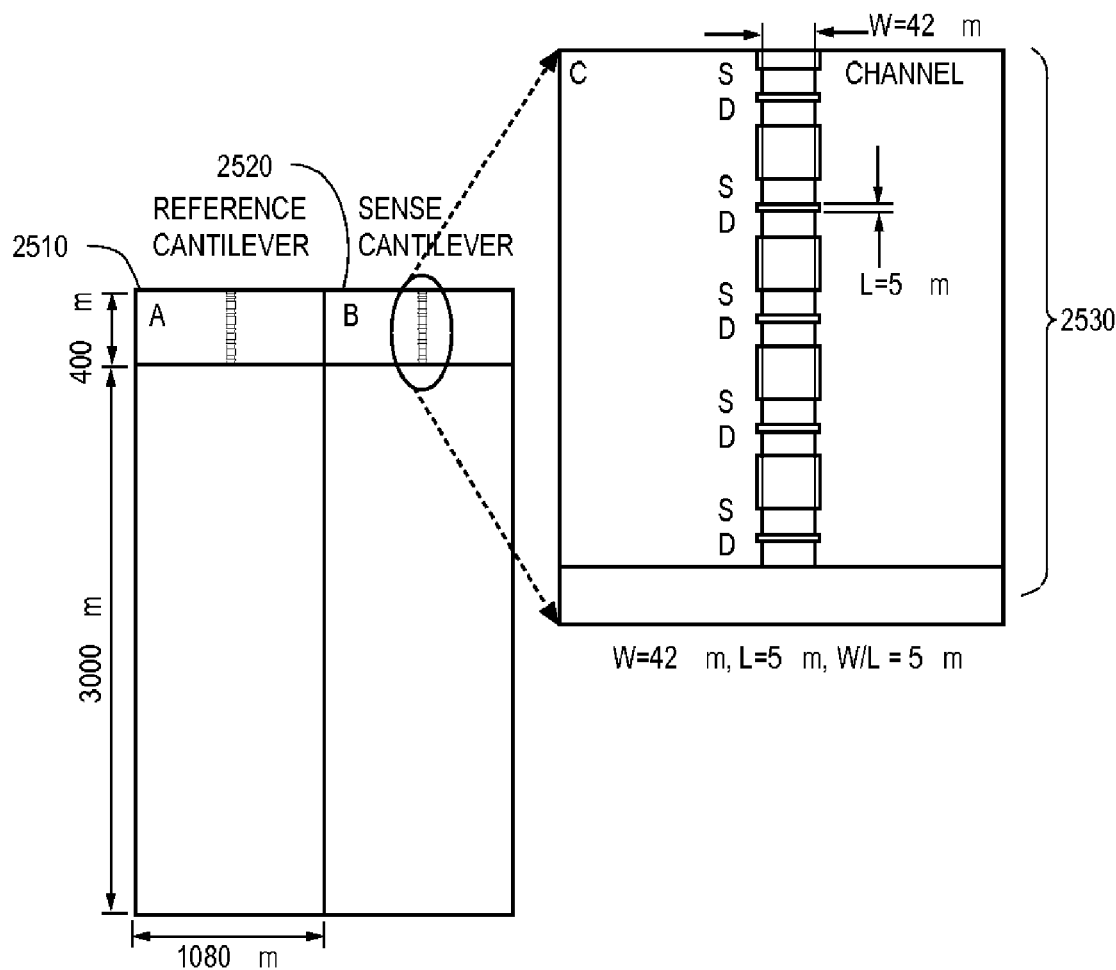
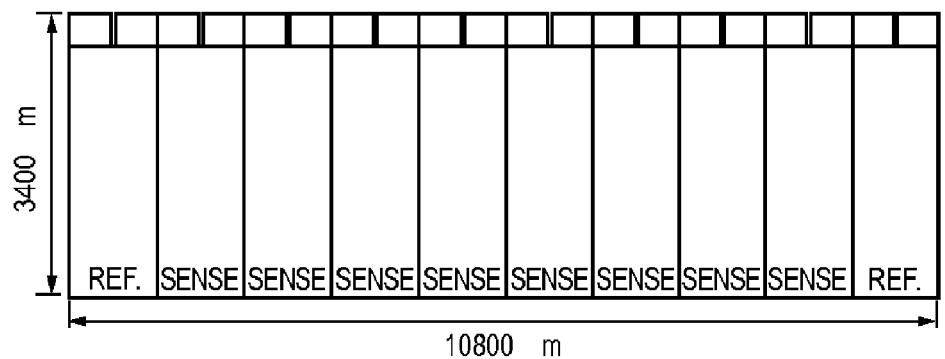

Fig. 26
CASCADED MOSFET EMBEDDED MULTI-INPUT MICROCANTILEVER
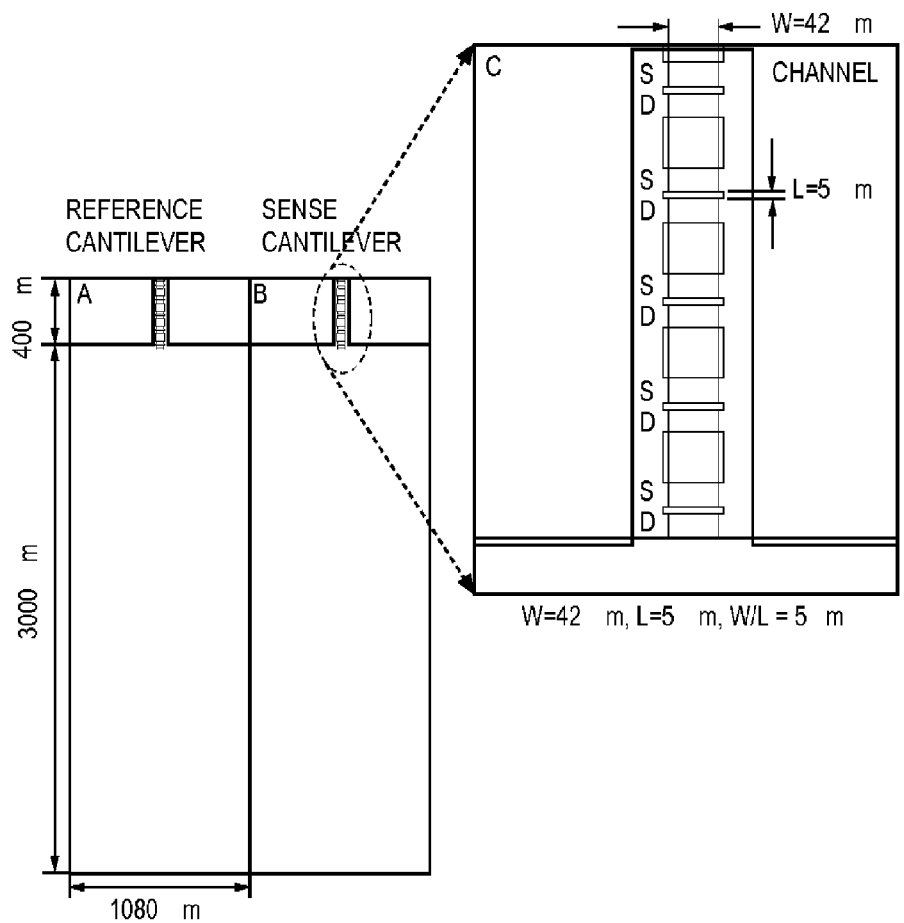
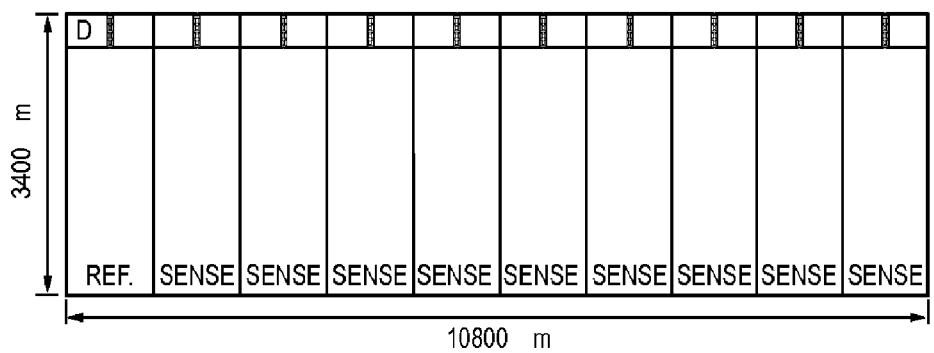

CASCADED MOSFET EMBEDDED MULTI-INPUT MICROCANTILEVER

CASCADED MOSFET EMBEDDED MULTI-INPUT MICROCANTILEVER

CASCADED MOSFET EMBEDDED MULTI-INPUT MICROCANTILEVER

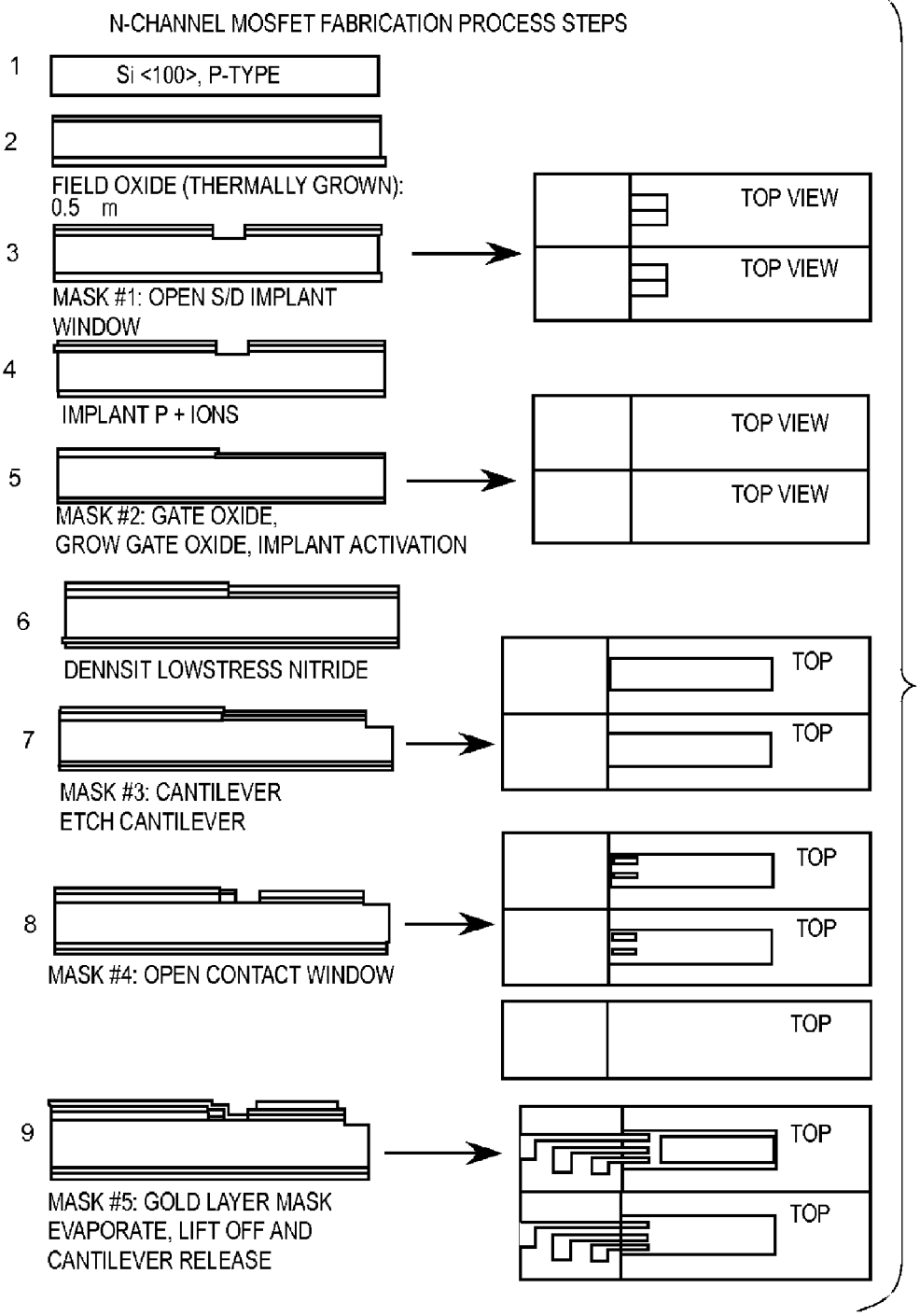

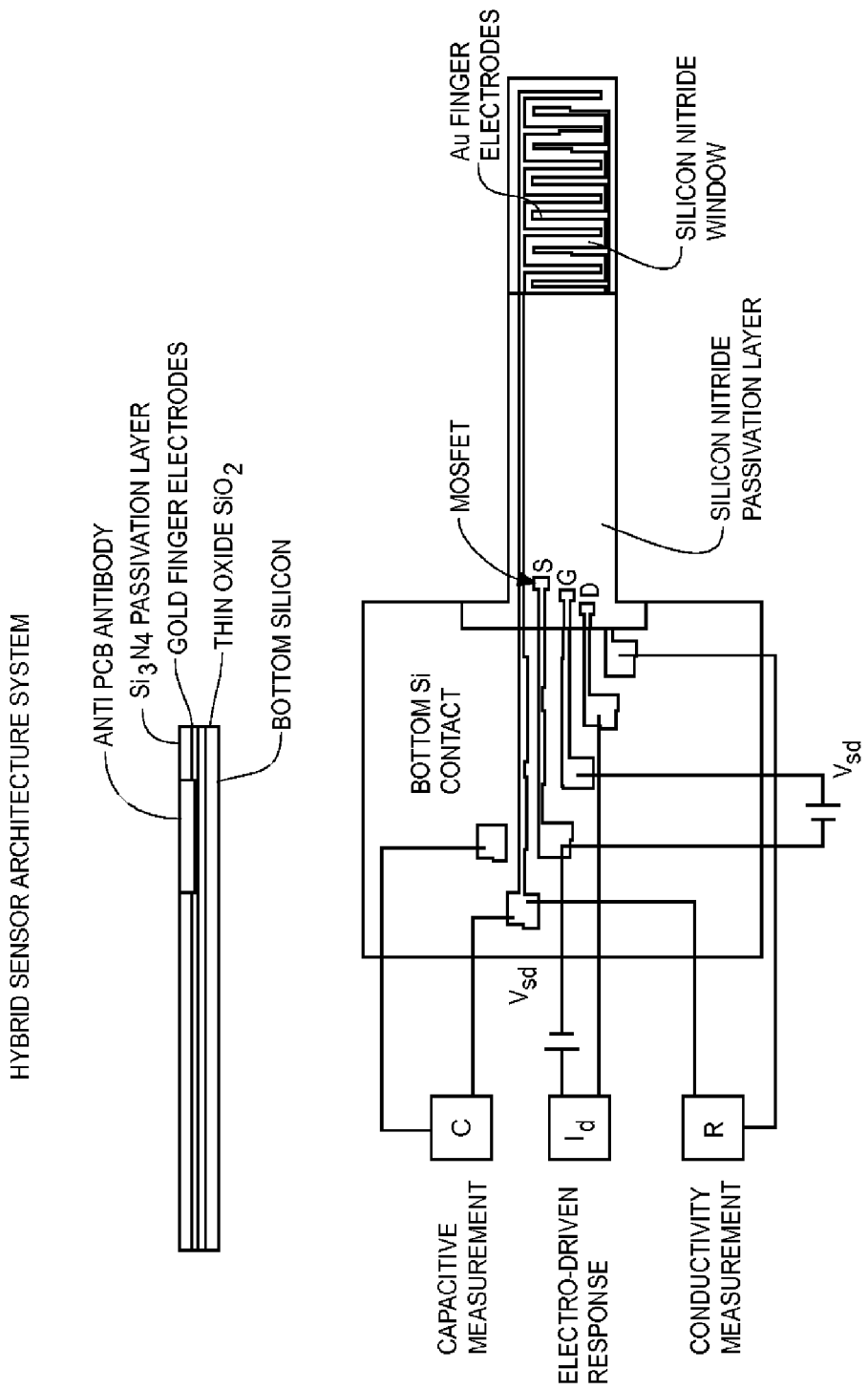

CASCADED MOSFET EMBEDDED MULTI-INPUT MICROCANTILEVER

CROSS-REFERENCE TO RELATED APPLICATIONS

The present application is a continuation-in-part of U.S. patent application Ser. No. 10/996,274, now U.S. Pat. No. 7,157,897 B2, filed Nov. 23, 2004, which claims benefit from and priority to U.S. Patent Application No. 60/524,994, filed Nov. 25, 2003. The above-identified applications are hereby incorporated by reference herein in their entirety.

STATEMENT REGARDING FEDERALLY SPONSORED RESEARCH OR DEVELOPMENT

This work was supported by the National Science Foundation (NSF) awards: # NSEC-EEC-0118025, and ECS-0330410, and Air Force Office of Scientific Research (AFOSR)-MURI # F49620-00-1-0283.

BACKGROUND OF THE INVENTION

Most biosensors and chemical sensors rely on specific molecular recognition events. See for example, G. Miller, W. C. Inkret, M. E. Schillaci, H. F. Martz, T. T. Little, Health Physics, Volume 78 (2000) 598; N. Iznaga, G. Nunez, J. Solozabal, A. Morales, E. Artaza, R. Rubio, E. Cardenas, Computer Methods and Programs in Biomedicine, Volume 47 (1995) 167; W. Gopel, Chemical imaging. 1. Concepts and visions for electronic and bioelectronics noises, sensors and actuators B, B52 (1998) 125; C. Nicolini, Thin solid films, Volume 284-285 (1996) 1; O. H. Willemsen, M. M. E. Snel, A. Cambi, J. Greve, B. G. Gooth, C. G. Figdor, Biophysical Journal, Volume 79 (2000) 3276 and M. Gomez-Lopez, J. A. Preece, J. F. Stoddart, Nanotechnology, Volume 7 (1996) 183. Specific molecular recognition events may be an antibody-antigen, DNA-DNA, or other ligand-receptor interactions. These recognition events are most commonly detected indirectly by various labeling techniques including radioactivity, enzymatic activity, visible markers, or fluorescent labels. See for example, M. Bras, J. Cloarec, F. Bessueille, E. Souteyrand, J. Martin, Journ. of Fluores., Vol. 10 (2000) 247. However, such techniques can be time consuming and often require relatively large, expensive instrumentation. Thus, there is a need for label free and continuous nanobiosensors for monitoring of bioaffinity interactions that can be easily integrated in array architecture on a CMOS chip. However, for most applications, arrays of currently available biosensors possess insufficient performance either due to large size, poor cross sensitivity, or long response times. Also, the majority of currently available biosensors are not compatible with complete CMOS Integration. Either the operation parameters of the biosensor are incompatible with CMOS, e.g. radioactive or fluorescence labeling, or the biosensor materials cannot be integrated within a CMOS process.

Recent efforts have focused on the development of cantilever-based sensors for the detection and transduction of chemical and biological processes. See for example, J. Fritz, M. K. Baller, H. P. Lang, H. Rothuizen, P. Vettiger, E. Meyer, H. J. Guntherodt, Ch. Gerber J. K. Gimzewski, Translating biomolecular recognition into nanomechanics, Science 288: 316-318 (2000); R. McKendry, J. Y. Zhang, Y. Amtz, T. Strunz, M. Hegner, H. P. Lang, M. K. Baller, U. Certa, E. Meyer, H. J. Guntherodt, C. Gerber, Multiple label-free bio-detection and quantitive DNA-binding assays on a nanomechanical cantilever array, PNAS 99: 9783-9788 (2002); Y. Amtz, J. D. Seelig, H. P. Lang, J. Zhang, P. Hunziker, J. P. Ramseyer, E. Meyer, M. Hegner, C. Gerber, Label-free protein assay based on a nanomechanical cantilever array, Nanotechnology 14: 86-90 (2003); R. Berger, E. Delmarche, H. P. Lang, Ch. Gerber, J. K. Gimzewski, E. Meyer, H. J. Guntherodt, Surface stress I the self assembly of alkanethiols on gold, Science, Vol. 276 (1997) 2021; S. J. O'Shea, M. E. Welland, T. A. Brunt, A. Ramadan, T. Rayment, Atomic force microscopy stress sensors for studies in liquids, J. Vac. Si. Technol., Volume B14 (1996) 1383; M. Tortonese, R. C. Barrett, C. F. Quate, Atomic resolution with an atomic force microscope using piezoresistive detection, Appl. Phys. Letters, Volume 62 (1993) 834. Through various physical or chemical mechanisms, biological and chemical processes may induce nanomechanical motion in a microfabricated Si cantilever array. For example, asymmetric (one-side only) molecular adsorption induces incremental surface stress, which produces a nanoscale deflection in high-Q ($>10^4$) cantilever systems. Because of their low mass and high Q-factors, these miniaturized sensors show fast response times, high sensitivity, and are suitable for mass production using standard IC fabrication.

In order to monitor cantilever deflection, an optical detector is employed to detect the reflection of a laser off of the tip of the cantilever. This technique offers excellent sensitivity to molecular adsorption. Moreover, well-established techniques of surface functionalization (chemical and biomolecular) provide a contrast mechanism for molecule-specific adsorption. However, the required optical system to measure cantilever deflection limits application to 10 s or 100 s of cantilevers and reduces its applicability to large (1000 s to 10,000 s) arrays. Optical-based techniques also require a relatively large amount of power (i.e. a dedicated lasers/detectors) and are less able to be miniaturized.

An electronic detection method for biomolecules using symmetrical wheatstone bridge configuration (piezo-resistive detection) is described in A. Boisen, J. Thaysen, H. Jensenius and O. Hansen, Environmental sensors based on micromachined cantilevers with integrated read-out, Ultramicroscopy 82 (2000) 11-16. In this design a full wheatstone bridge was placed symmetrically on a chip. Two adjacent cantilevers comprise two of the bridge resistors. The second two resistors are placed on the substrate (via doping by Ion-implantation). This design enables differential measurements where the signals from the two cantilevers are subtracted. The relative resistance change of the piezo-resistor ($\Delta R/R$) will be detected as an output voltage ($V_o$) from the wheatstone bridge with a supply voltage (V). The output voltage can be written as $V_0 = \frac{1}{4}V\,(\Delta R/R)$. A differential amplifier will amplify the differential signal to improve the sensitivity of the cantilevers. Unfortunately, this detection method has a number of technological problems. One problem relates to non-linearities in the measurements. Another problem is serious low frequency noise. The cantilever bends by a few nanometers upon adsorption induced surface stress, so that even small noise issues cripple the validity of the measurements. A further problem is concerned with the difficulty of integration on a CMOS platform, which is required for miniaturization and on chip signal transmission and detection.

Utilizing combined electrical sensing and actuation of Si micro-cantilevers has been demonstrated in atomic force microscope imaging of materials such as graphite. See for example, S. Minne, G. Yaralioglu, S. Manalis, J. A. Adams, C. Quate, Appl. Phys. Lett., Vol. 72 (1998) 2340; S. C. Minne, S. R. Manalis, C. F. Quate, Integrated piezo-resistive and piezo-actuator based parallel scanning probe microscope, Appl.

Phys. Letts., Volume 67 (1995) 3918. In this device, polysilicon-based piezo-resistors are put on a cantilever and an integrated piezo-actuator. This device suffers from thermal and electrical noise issues. Low frequency noise is a very critical parameter. Significant noise problems make feedback tracking unstable and can result in crashing of the cantilever with the surface of the material being imaged.

BRIEF SUMMARY OF THE INVENTION

In accordance with the present invention, the disadvantages of prior sensors as discussed above have been overcome. The sensor of the present invention detects mechanical perturbations by a change in an electrical signal.

More particularly, the sensor includes a structure and a field effect transistor embedded in the structure wherein the transistor has an associated electrical current that changes with mechanical perturbations in the structure.

In another embodiment of the present invention, the sensor includes a first structure with a first field effect transistor embedded therein, the first structure having a surface coated with a material to which a probe molecule will adhere. The sensor also includes a second structure used as a reference with a second field effect transistor embedded in the second, i.e. reference, structure. The first and second field effect transistors are coupled to a differential amplifier to provide an electrical signal indicative of mechanical perturbations in the first structure caused by target molecules binding to probe molecules on the first structure.

In a further embodiment of the present invention, the sensor includes a structure and a field effect transistor embedded in the structure, the transistor providing an electrical signal that changes with mechanical perturbations in the structure. The sensor also includes a piezo-actuator on or embedded in the structure to provide bending and a feedback circuit that is coupled to the transistor and is responsive to the transistor's electrical signal to control the actuator.

In a further embodiment of the present invention, a plurality of field effect transistors may be cascaded and embedded in a structure to form a sensor for detecting mechanical perturbations represented by a change in an electrical signal.

In a further embodiment of the present invention, a plurality of microcantilevers are arranged to create an array of microcantilevers including at least one reference microcantilever and at least one sense microcantilever. A plurality of cascaded MOSFETs are embedded in each of the microcantilevers to detect mechanical perturbations represented by a change in an electrical signal.

These and other advantages and novel features of the present invention, as well as details of several illustrated embodiments thereof, will be more fully understood from the following description and drawings.

BRIEF DESCRIPTION OF THE SEVERAL VIEWS OF THE DRAWING

FIG. 7 is a top cross-sectional view of a MOSFET embedded microcantilever in accordance with one embodiment of the present invention;

FIG. 15 is a graph illustrating time dependent drain current vs. drain voltage measurement for streptavidin and 50 nM biotin binding at Gv=1.0V;

FIG. 16 is a graph illustrating drain current vs. time for streptavidin and 50 nM biotin binding at Gv=1.0V and three different drain voltages;

FIG. 25 illustrates an exemplary design process for a cascaded MOSFET-embedded multi-input microcantilever.

FIG. 26 illustrates an exemplary design process for a cascaded MOSFET-embedded multi-input microcantilever.

FIG. 39 shows an exemplary process layout for embedded BiMOS cantilevers.

FIG. 43 shows an exemplary hybrid sensor architecture system.

DETAILED DESCRIPTION OF THE INVENTION

Figure 1:
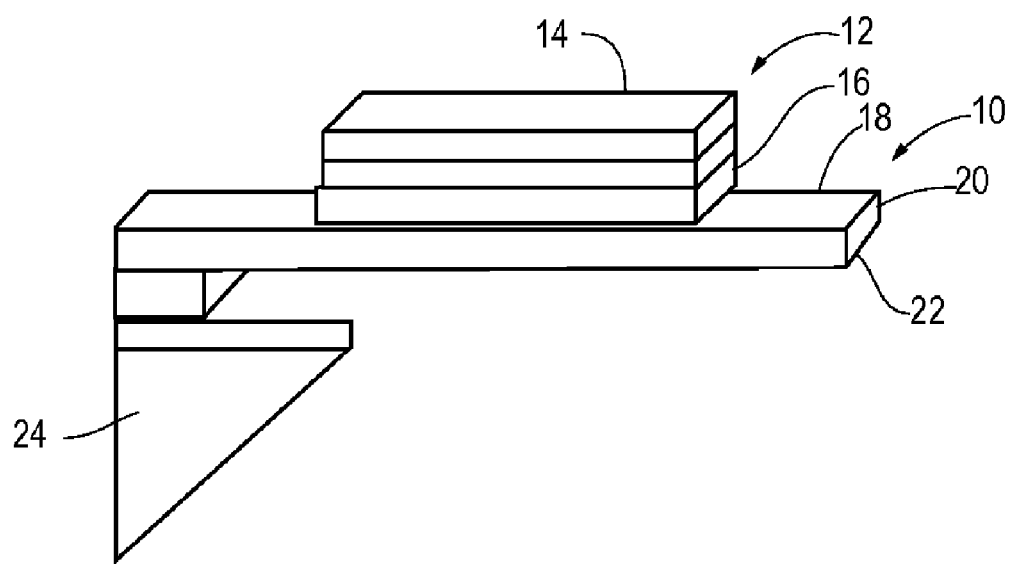
FIG. 1 is an illustration of an integrated actuator in the form of a BiMOS transistor on a cantilever for use in a nanosensor in accordance with the present invention.

The present invention relates to a novel sensor system based on silicon chip technology for electronic detection of molecular interactions. The present invention has ultra-high sensitivity, extremely low noise density and a cost effective technology platform and provides a powerful and easy to handle biological and chemical nanosensor for molecular and dangerous threat agent detection at ppb or ppq scale.

In accordance with one feature of the present invention, the sensing element is an integrated MOSFET (Metal Oxide Semiconductor Field Effect Transistor) transistor combined with a bipolar transistor, where the sensing element is placed at a high stress region of the microcantilever. The combined circuit of MOSFET and bipolar transistors is called BiMOS. The BiMOS platform not only has improved sensitivity, but also has an almost negligible noise figure (large signal to noise ratio), and ease of integration with CMOS and RF components. The micro-cantilever is immobilized with antibodies or a chemical sensitive layer. Upon interaction with threat agents, the cantilever bends due to either compressive or tensile stress resulting in a change in the drain current of the MOSFET chip. The bipolar transistor converts current to a voltage and amplifies the signal so as to eliminate the need for further functions in the amplification circuits. Multi-arrays with an integrated BiMOS chip embedded in them can act as a fingerprint for detection of toxic agents.

In accordance with another feature, the present invention relates to an integrated electric piezo-actuator and BiMOS electronic detector on the cantilever chip. The BiMOS output signal acts as a feedback signal to keep a constant separation between the cantilever and the surface of the material being imaged, thereby eliminating the need for optical detection of cantilever deflection. This feature will allow multi-parallel operation of the Scanning Probe Microscope which is not possible with current optical detection method.

Advantages of the present invention include (1) ease of integration with Si chip technology; (2) robust and highly sensitive detection; (3) cost-effective chip technology; (4) miniature size; (5) multi-analyte detection using a single platform; (6) arrayed readout with high sensitivity and ultra low noise density; (7) common mode rejection for noise cancellation; (8) wide dynamic range and easily integrated RF circuits; (9) low power electronics, power management circuitry and electrical self testing; and (10) single step label free assay, i.e. there is no need for fluorescent or radioactive labels, which reduces the amount of reagents required as well as the time for each reaction.

More particularly, in accordance with one feature of the present invention, sensing elements for biological and chemical agents use an array of micro-cantilever(s) with on-chip fabricated BiMOS electronic readout fabricated using CMOS technology. BiMOS readouts provide ultra-high sensitive detection of biomolecular and chemical interactions on the cantilever surface with very low noise density and ease of integration with microelectronics platform. Multiple arrays of such micro cantilevers will have potential applications for on-chip electronic noise. In accordance with another feature of the present invention, the cantilever comprises two sections: an actuator section, which includes an actuator that is located relatively near the fixed base of the cantilever; and a bending section, which is associated with a deflection detector and is located relatively near the free end (tip) of the cantilever. The actuator controls the position of the tip relative to the sample. The detector is a BiMOS electronic reader that detects the deflection of the cantilever. More particularly, the detector is a BiMOS readout, which provides a noise free feedback signal to maintain the cantilever at a constant distance from the surface of the material being imaged. Low noise feedback is of extreme importance in properly tracking the surface of the sample and measuring nm scale deflection of probes. This may help open completely new vistas in fabricating high frequency multi-active probes for developing high speed scanning probe microscopy imaging, patterning and analysis paradigm. Integrated piezoactuators will provide the necessary actuation of cantilever and drive it in resonance. It will provide the high speed AC mode detection of surface features.

The sensing element of the present invention as shown in FIG. 1 includes a micro-cantilever 10 with an integrated piezo-actuator 12. A BiMOS transistor is formed on or embedded in the micro-cantilever 10 as discussed below. These sensing elements may be used as Scanning Probe Microscopy Probes. The piezo-actuator 12 includes ZnO piezos having metallic contacts 14 and 16. The contact 16 is placed on a silicon dioxide layer 18 of the cantilever 10. The cantilever 10 also has a silicon nitride layer 20 and a second silicon dioxide layer 22. A probe 24 also includes a silicon dioxide layer 26.

Surface processes such as molecular adsorption/desorption can induce a stress, either tensile or compressive. In both cases, if the stress changes only on one side of a thin-cantilevered beam, the beam will permanently bend. The cantilever can therefore transduce a molecular/biomolecular adsorption at a single cantilever surface into a measurable mechanical deflection. The relationship between single-sided surface stress change, $\Delta\sigma$, and the resulting change in static deflection, $\Delta z$, is related by the following equation:

$$\Delta z \cong \frac{3(1-v)}{E} \frac{L^2}{t^2} \Delta\sigma$$

Where L and t are cantilever length and thickness and E and v are the Young's modulus and Poisson's ration, respectively, of the cantilever material. Surface adsorption processes (e.g. molecular/biomolecular adsorption) can therefore be sensed by measuring cantilever deflection. For a given material, stress sensitivity is proportional to the square of the length to thickness ration $(L/t)^2$. However, cantilevers are affected by external mechanical noise, which is damped by a factor proportional to $(f_{ext}/f_o)^2$ where $f_{ext}$ is the noise frequency and $f_0$ is the fundamental mechanical resonance frequency of the system. For optimal performance this resonance should be as high as possible. In the case of a rectangular cantilever the resonance frequency is given by:

$$f_0 \alpha \sqrt{\frac{E}{P} \frac{t}{L^2}}.$$

In order to maximize the overall sensitivity of the cantilever to stress-induced deflection, it is necessary to optimize $(L/t)^2$ and $(t/L^2)$ simultaneously. Miniaturizing the cantilever dimension aids this process via the high Q-factors of micromachined Si structures. Microfabrication technologies will allow fabricating micrometer-sized cantilevers with high length to thickness ratio in a reproducible and inexpensive fashion. The dynamic response to such cantilevers is also well understood. The resonance frequency shift of an apex-loaded cantilever is a well-defined function of the loading, m where $$m = \frac{K}{4n\pi} \left( \frac{1}{f^2} - \frac{1}{f_0^2} \right).$$

K is the spring constant, n is the geometry dependent correction factor and $f_0$ and $f_1$ are the resonance frequencies of the unloaded and loaded sensor, respectively. For K on the order of 1 N/m and $f_0$ on the order of 100 kHz, the theoretical resolvable mass loading is on the order of femtograms.

To properly account for these fundamental mechanical properties the performance of the multifunctional cantilever sensor can be modeled and simulated through a joint effort of SPICE®, ANSYS® and Intellisuite® finite element analysis (FEA) programs. Optimization of cantilever width, thickness and resonance frequencies can be carried out with these software packages. Specific cantilever designs are targeted to optimize stress localization at the base of the cantilever for subsequent measurement via a MOSFET detector integrated with bipolar transistor as discussed below. In addition, a resonance frequency analysis of various cantilever designs can be carried out to analyze and optimize effects of mass loading. The FEA simulations reduce the need to perform detailed experimental optimization of the device characteristics. The lengths of the cantilevers in simulations that have been performed ranged from 200 to 450 µm and the thickness of the cantilevers in the simulations ranged from 1.5 to 3.0 µm. It has been found that maximum stress is generated at the base of the cantilever. This area is referred to as the stress concentration region (SCR). These simulated results guide in the placement of the piezo-resistor or BiCMOS actuator on the cantilever at a maximum in the SCR.

Figure 2:
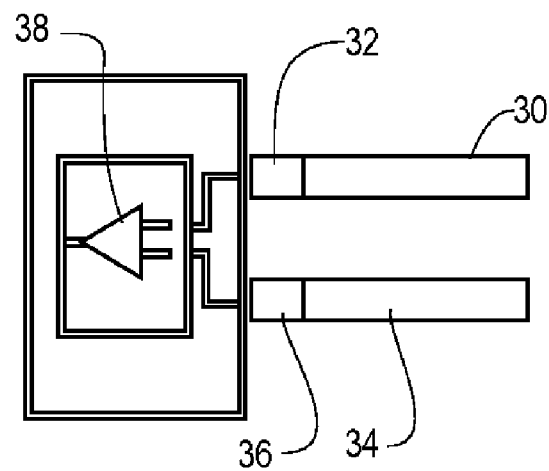
FIG. 2 is an illustration of an electrical schematic representing the integration of BiMOS electronic readout and actuator on cantilevers in a two cantilever configuration.

The electronic detection of bimolecular signals use a BiMOS electronic readout integrated on micro-cantilever arrays. Built-in background filters are also integrated on the high stress region of the cantilever. Cantilever fabrication employs SOI wafers with buried oxide etch-stop layers, to provide probes with fully encapsulated BiCMOS resistors. The dimension of the resistors are defined and appropriate processes optimized to minimize leakage currents. Cantilevers with a force constant in the range of 1-5 N/m and with resonant frequencies in the range of 50-200 kHz are targeted for fabrication. The electronic configuration of the BiMOS chip is shown in FIG. 2. In this configuration, a Si sensor cantilever 30 has an integrated or embedded BiMOS reading or sensing element 32 that provides an electronic readout as described below. A Si reference cantilever 34 also has an integrated BiMOS transistor 36 as described below. Each of the BiMOS transistors 32 and 36 are coupled to a CMOS Differential Amplifier 38 to provide an output. The primary advantage of the present invention is the lower noise figure associated with a combination of a MOS and a bipolar (BiMOS) stress transistor as compared to wheatstone bridge configuration and the ease of integration with RF and BiCMOS components on a chip.

The drain-source current of the embedded BiMOS transistor is biased in the saturation region and can be easily modulated with mechanical stress in the conducting channel. See for example, D. Colman, R. T. Bate, J. P. Mize, Journal of Appl. Phys., Volume 39 (1968) 1923. The relative change in the source-drain current of a BiMOS transistor under stress is a function of the piezo-resistive coefficient $\pi$ of the inversion layer and the stress $\sigma$: $\Delta I_d/I_d = -\pi\sigma$. The size of the BIMOS stress transistor will be maximized to minimize 1/f noise. The advantage of using BiMOS is two folded. First, high current sensitivity of the MOS transistor will be utilized to detect molecular interactions in ppt or ppq scale. Secondly, high frequency bipolar transistors will convert the current into a voltage signal and amplify it to have further high fan out capability. In other words, as bipolar transistors are high power devices, they can further drive more electronic circuits on the chip. Moreover, bipolar transistors have minimal low frequency noise. The unique combination of a MOS and a bipolar transistor will provide a noise free detection of toxic ions.

Figure 3:
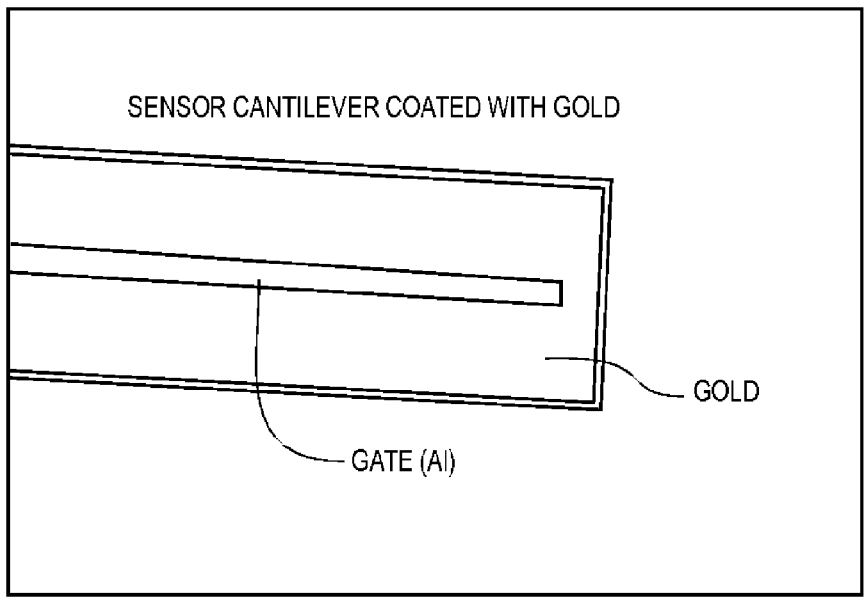
FIG. 3 is an illustration of a cantilever with an integrated BiMOS electronic read-out.
Figure 4:
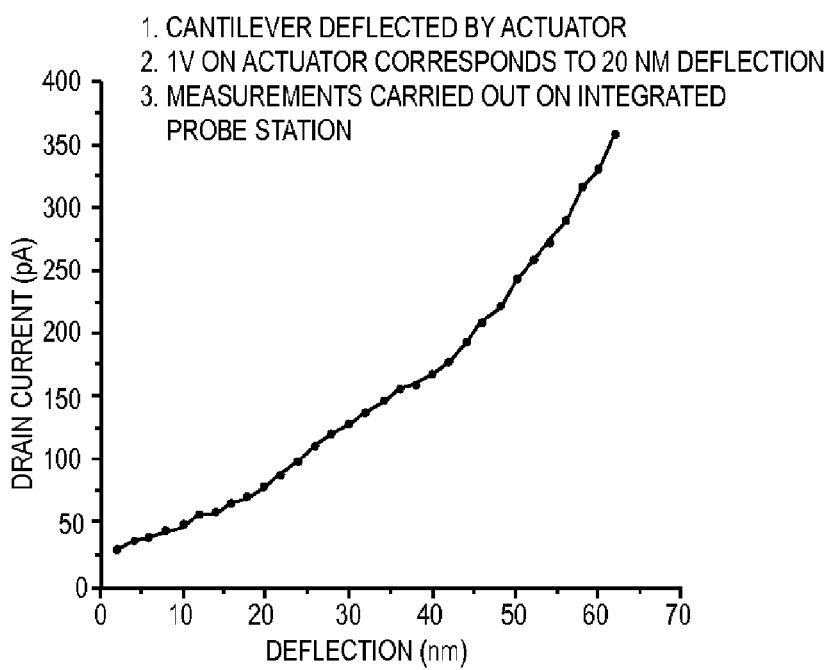
FIG. 4 is a graph of the current versus voltage characteristics of the BiMOS piezo-actuator after the cantilever is deflected.
Figure 5:
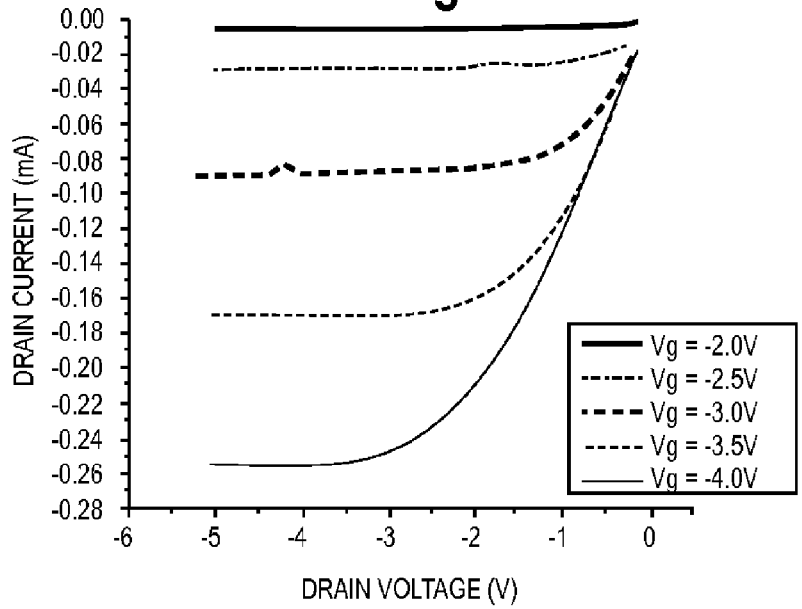
FIG. 5 is a graph of the normal characteristics of a MOSFET transistor.

A first proof of concept device was successfully fabricated. Initially, only embedded MOSFET readouts were put on the fabricated cantilever structures as shown in FIG. 3. These cantilevers were used in the two-cantilever configuration of FIG. 2 where one of the cantilevers is designated as reference and the other cantilever is designated as a sensor cantilever. Standard MEMS technology was used to fabricate these cantilevers. In this device geometry, MOS field effect transistors are formed on the high stress region of the cantilever. Electrical testing can be carried out using an integrated probe station in order to verify the performance characteristics of the embedded MOSFET electronic readouts. FIG. 4 shows the current vs. voltage plot for one of the MOSFET embedded in the cantilever. The actuator physically bent the cantilever. Initial results clearly indicate that the transports can detect 1 nm of cantilever deflection. Out current sensitivity, $\Delta I/I$, was approximately $10^{-6}$, which is quite close to that for optical detection. Electrical measurements were also carried out for testing the embedded MOSFET device and results are depicted in FIG. 5.

Figure 6:
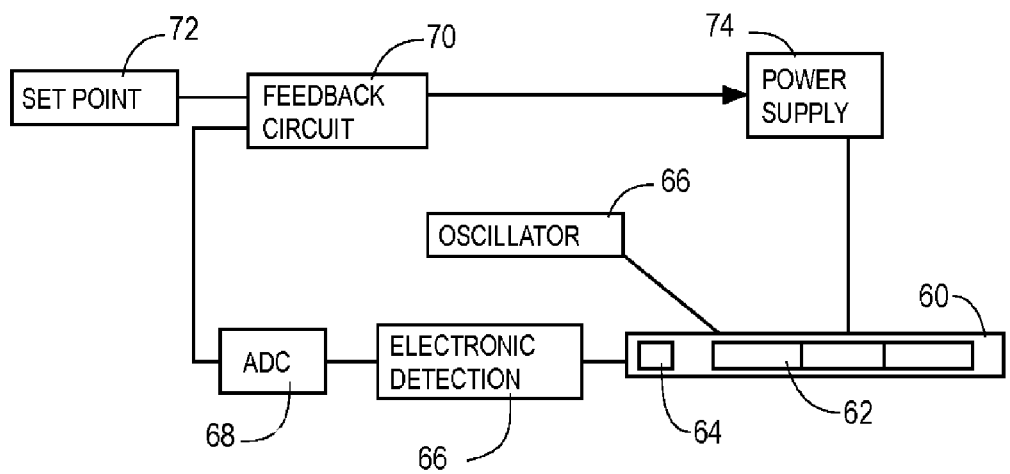
FIG. 6 is a block diagram of a feedback controlled integrated cantilever.

A noise free parallel Scanning Probe Microscope (SPM) using multi arrays of cantilevers with integrated highly sensitive BiMOS transistors for actuation and electrical detection of cantilever deflection is shown in FIG. 6. As shown therein, a Si cantilever 60 has an integrated piezo-actuator 62 and a BiMOS electronic readouts 64. An oscillator 66 is coupled to the actuator 62 to drive the actuator. The BiMOS readouts 64 is coupled to an electronic detection circuit 66, the output of which is coupled to an analog-to-digital converter 68. The output of the analog-to-digital converter 68 is coupled to a feedback circuit 70 to which a set point 72 is also coupled. The output of the feedback circuit is used to adjust the power supply voltage 74 applied to the Au contacts of the actuator 62. The electrical detection and feedback control will allow the SPM to have multiple arrays, which will scan a whole 100 mm wafer in a span of few seconds. High frequency integrated actuators will increase the speed of the scanning and individual control of each cantilevers in an array. The present invention may be used in parallel SPM for imaging surface structures, dip pen nanolithography and nanopatterning, where one can control physical dimensions of individual pattern.

FIG. 7 illustrates a sensor 80 for detecting mechanical perturbations in a structure, such as a cantilever 82, with a field effect transistor, that is preferably MOSFET embedded in the cantilever structure 82, such that the transistor provides an electrical signal or readout that changes with mechanical perturbations in the cantilever 82. Specifically, mechanical perturbations in the cantilever 82 result in a change in the drain current of the embedded BiMOS or MOSFET. For example, when the sensor 80 is used for bio-chemical sensing, the cantilever bends due to either compressive or tensile stresses caused by an interaction between target molecules and probe molecules on the cantilever as discussed below. Multi-arrays with integrated BiMOS chips embedded therein can act as a fingerprint for the detection of for example, toxic and biological agents. The embedded BiMOS is a means of detecting change in nanomechanics, e.g. bending, vibrations etc., and can be applied not only to microcantilevers but to other structures which require a detection scheme for mechanical stress or deflection such as cantilever arrays, membranes, MEMS devices, etc. Moreover, the sensor is not limited to conventional Si transistors as discussed below. The invention also applies to other forms of field effect transistors, including polymer/organic, SiC/GaN, nanotube, etc., types of field effect transistors.

Figure 8A:
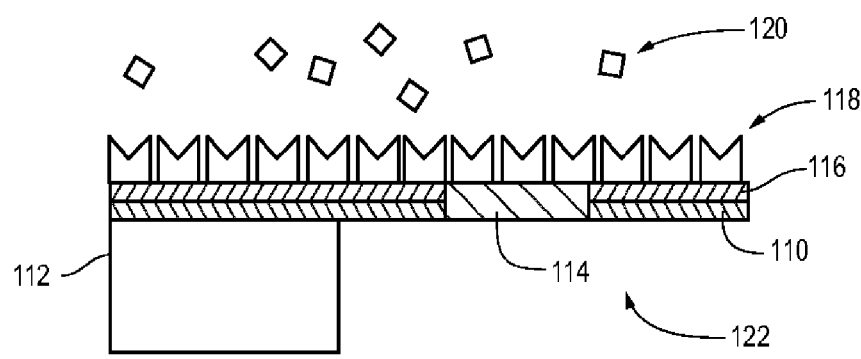
FIGS. 8A-B is a side cross-sectional view of a MOSFET embedded microcantilever with probe molecules and target molecules illustrated.
Figure 8B:
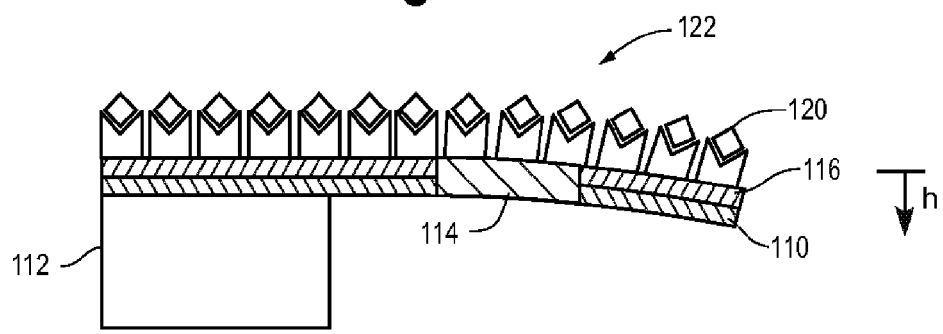

The structure shown in FIG. 7 is a NMOS structure wherein the embedded MOSFET has a N+ drain contact formed of Al 84 and a N+ source contact 86 similarly formed of Al. The N+ drain contact 84 extends from a gold, i.e. Au, contact 88 to a P-type drain 90. The N+ source contact extends from a gold contact 92 to a P-type source 94 on the cantilever 82. The gate 96 of the MOSFET shown in FIG. 7 is formed of an Al contact that extends from a gold contact 98 on the silicon base 100 to a free end 102 of the cantilever 82. The layer by layer details of the sensor 80 of FIG. 7 are as follows. First, a three micron epi Si layer forms a base of the sensor. Next, a 100 nm oxide layer is formed on the Si layer. Thereafter, the P-type source and drain regions 94 and 90 are formed in a third layer. The fourth layer includes the Al contacts for the source 86 and the drain 84. The fifth layer includes a 20 nm gate oxide and the sixth layer includes 100 nm SiN layer. In a seventh layer, the Al contact 96 for the gate of the MOSFET is formed. The eighth or top layer is formed by a gold or Au coating on the whole cantilever or with the exception of the Al contact for the gate when the structure is used as a probe structure as discussed below. Although a NMOS sensor is shown in FIG. 7, by changing the doping, a PMOS sensor can be formed. A PMOS structure creates less flicker noise due to low mobility and a large gate area in order to suppress 1/f noise. Cross-sectional views of a MOSFET embedded microcantilever for detecting biomolecular interactions are shown in FIGS. 8A and 8B. FIGS. 8A and 8B show a MOSFET 114 embedded in an cantilever 110, such as a cantilever described in G. Wu, R. Datar, K. Hansen, T. Thundat, R. Cote and A. Majundar, Nature biotechnology 19, 856 (2001). The cantilever 110 is a silicon nitride microcantilever with an embedded MOSFET 114 as described above. The microcantilever 110 is supported on a silicon base 112 and has a coating 116 of gold on a surface of the microcantilever 110. In order to use the sensor 122 to detect a toxic agent, for example, the sensor 122 is dipped in a solution of probe molecules 118 where the probe molecules are antibodies of the toxic agent that is being tested for. Thereafter, the sensor 122 is dipped in a solution of the target molecules 120 that are being tested for. If the target molecules 120 bind to the probe molecules 118, stress is induced in the cantilever 110 causing the cantilever to bend either up or down as shown in FIG. 8B indicating that the toxic agent being tested for is present in the target solution. The relationship between single-sided surface stress change, σ, and the resulting change in static deflection, σZ, is related by the following equation as discussed above.

$$\Delta z \cong \frac{3(1-v)}{E} \frac{L^2}{t^2} \Delta \sigma$$

The change in σ induces a change in the drain current $i_d$ of the embedded MOSFET 114 so as to provide an electrical signal and electrical readout representing the mechanical perturbations in the cantilever 110 caused by target-probe binding. In this example, the deflection of the cantilever indicates the presence of the target molecule in the solution being tested.

Figure 9:
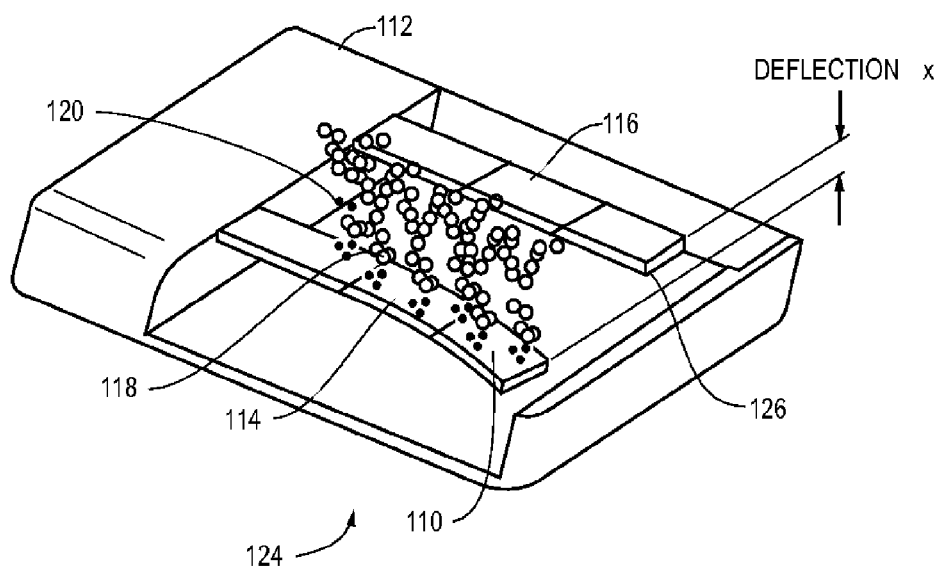
FIG. 9 is a perspective view of a sensor having a probe cantilever and a reference cantilever with probe and target molecules illustrated.
Figure 10:
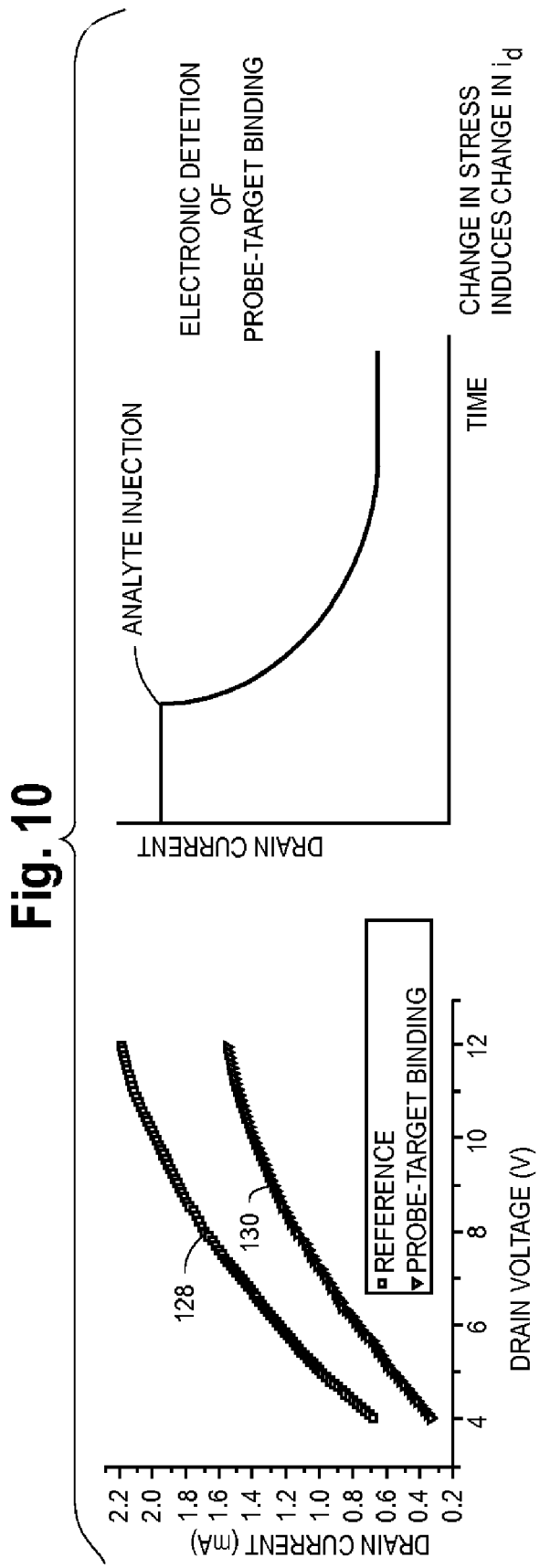
FIG. 10 is a graph illustrating drain current vs. voltage and time for the sensor of FIG. 9.

As shown in FIG. 9, the sensor 124 includes a probe microcantilever 110 with embedded MOSFET 114 as discussed above with reference to FIGS. 8A-B. The sensor 124 also includes a reference cantilever 126 with an embedded MOSFET 116. Both of the cantilevers 110 and 126 are formed of silicon nitride with the various layers described above with reference to FIG. 7. However, the cantilevers differ in that the probe cantilever 110 has the gold or Au coating whereas the reference cantilever 126 does not have the gold coating. Because the reference cantilever 126 does not have the gold coating, when the sensor 124 is dipped in a solution of probe molecules 118, the probe molecules do not adhere to the reference cantilever 126 but will adhere to the probe cantilever 110. Thereafter, when the sensor 124 is dipped in the solution to be tested, if the target molecules are present, the target molecules will bind to the probe molecules on the probe cantilever 110, but the target molecules will generally not bind to the reference cantilever 126. In this embodiment, each of the transistors 114 and 116 is coupled to a CMOS differential amplifier as discussed above to provide an electronic readout that represents the difference in the induced stress in the cantilevers 110 and 126. The reference cantilever 126 is used to nullify bending of the cantilevers 110, 126 that results from other than the target molecules being tested for. FIG. 10 illustrates the drain current vs. drain voltage and drain current vs. time for the electronic detection of probe target binding as discussed above with reference to FIG. 9. More particularly, the graphs 128 represents the drain current vs. drain voltage for the reference transistor 116 whereas the graph 130 represents the drain current vs. drain voltage for the transistor 114 with probe target binding.

Figure 12:
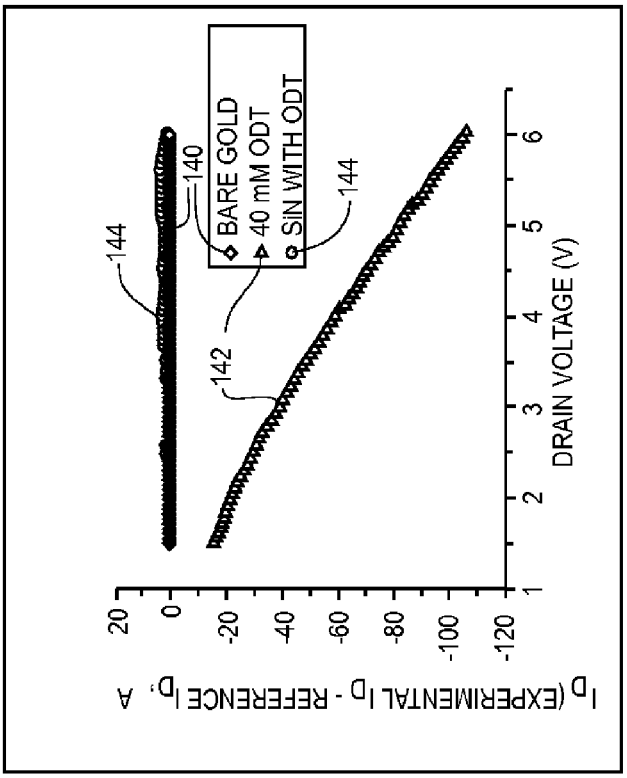
FIG. 12 is a graph illustrating the change in drain current vs. drain voltage for ODT detection.
Figure 11:
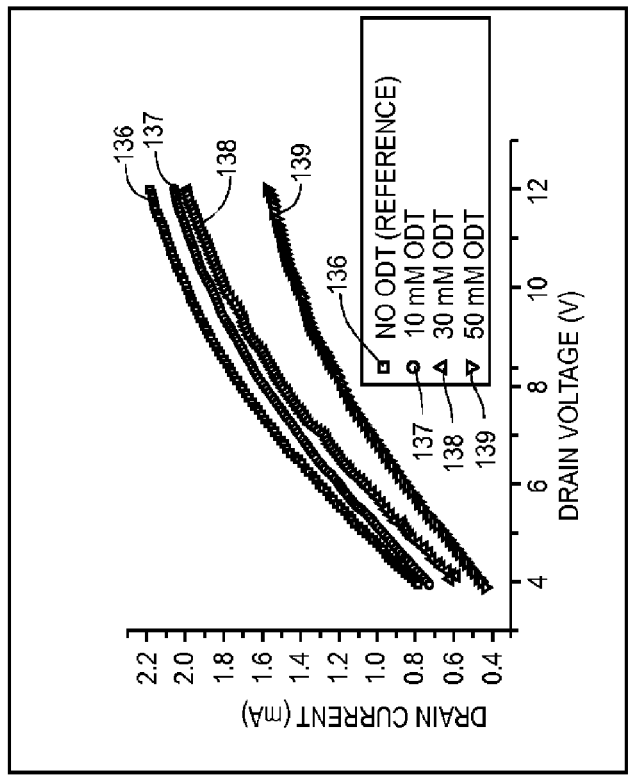
FIG. 11 is a graph illustrating drain current vs. drain voltage for different ODT concentration.
Figure 14:
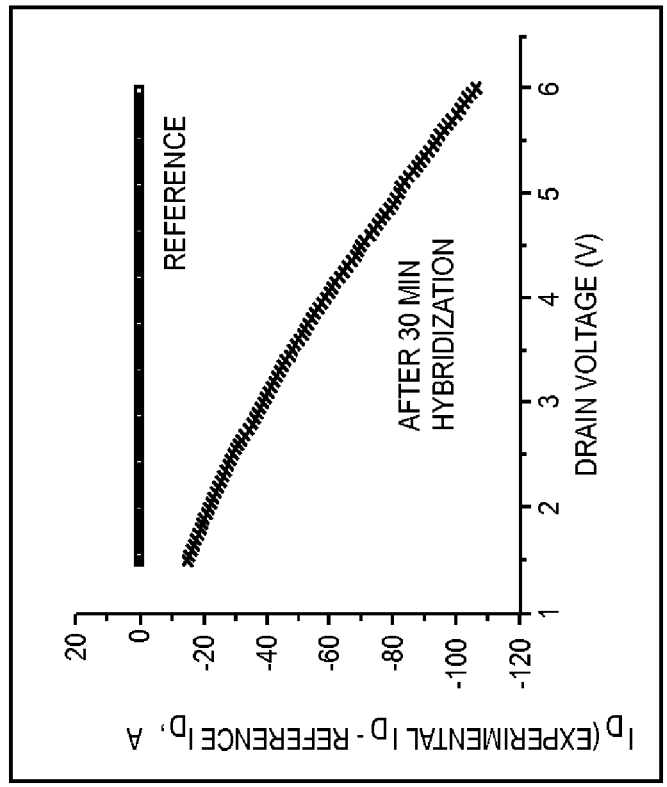
FIG. 14 is a graph illustrating the change in drain current vs. drain voltage for the electronic detection of DNA hybridization.
Figure 13:
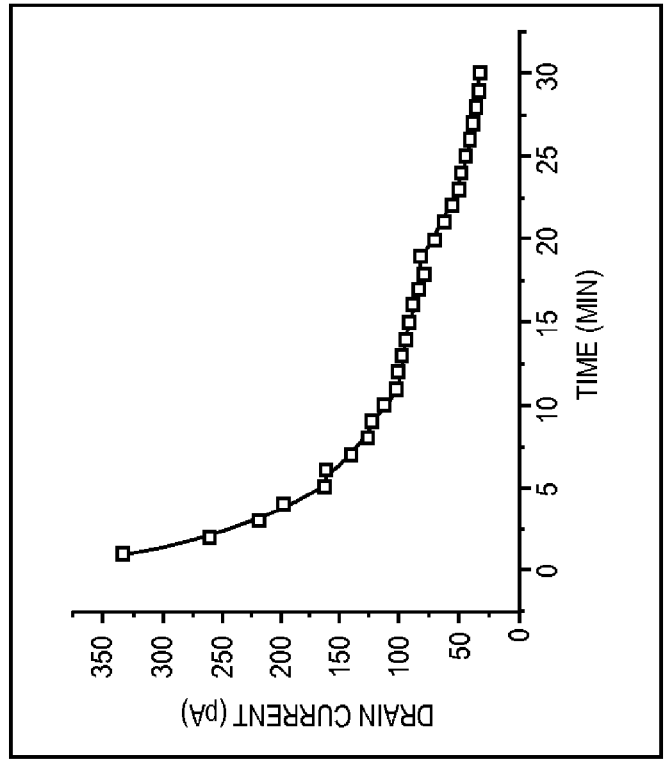
FIG. 13 is a graph illustrating drain current vs. time for the electronic detection of DNA hybridization.
Figure 18:
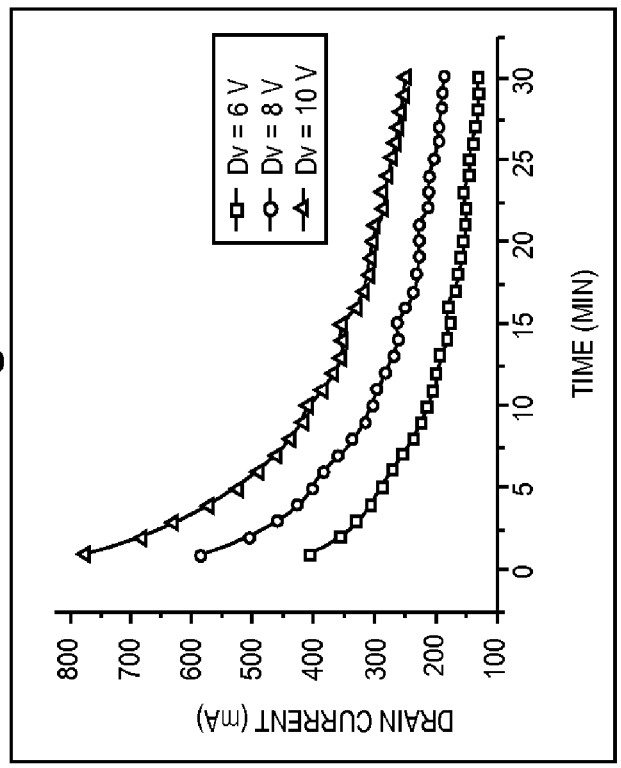
FIG. 18 is a graph illustrating drain current v. time for three different drain voltages for the electronic detection of Atrazine Antigen-antibody binding.
Figure 17:
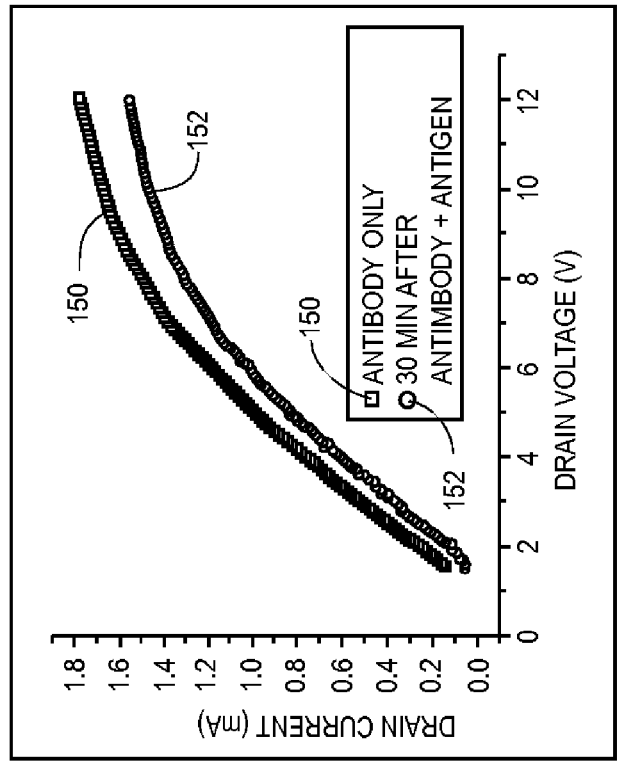
FIG. 17 is a graph illustrating drain current vs. drain voltage at Gv=1.0V for the electronic detection of Atrazine Antigen-antibody binding.

FIGS. 11 and 12 illustrate ODT detection using a MOSFET embedded cantilever sensor as discussed above. More particularly, FIG. 11 illustrates the drain current vs. drain voltage for different ODT concentrations at Gv=1.5V. FIG. 12 illustrates the change in drain current vs. drain voltage at Gv=1.0V. The graph 136 represents no ODT; the graph 137 illustrates 10 mM ODT; the graph 138 illustrates 30 mM ODT and the graph 139 illustrates 50 mM ODT. In FIG. 12, the graph 140 represents bare gold, the graph 142 represents 40 mM ODT and the graph 144 represents SiN with ODT. FIGS. 13 and 14 depict electronic detection of DNA hybridization. Specifically, FIG. 13 depicts the drain current vs. time for 40 nM target ssDNA hybridization at Gv=1.0V and Dv=6.0V. As shown, drain current decreases with hybridization time and reaches saturation in approximately 30 minutes. FIG. 14 shows the change in drain current vs. drain voltage at Gv=1.0V for 40 nM target ssDNA. FIGS. 15 and 16 illustrate electronic detection of streptavidin-biotin binding. Specifically, FIG. 15 depicts the time dependent drain current vs. drain voltage measurement for streptavidin and 50 nM biotin binding at Gv=1.0V. FIG. 16 illustrates the drain current vs. time for streptavidin and 50 nM biotin binding at Gv=1.0V and three different drain voltages. FIGS. 17 and 18 illustrate the electronic detection of Atrazine Antigen-antibody binding. More particularly, FIG. 17 illustrates the drain current vs. drain voltage at Gv=1.0V for an antibody only 150 and at 30 minutes after the antigen-antibody binding at 152. As can be seen, drain current decreases with antigen (0.1 mg/ml) antibody (0.1 mg/ml) binding. FIG. 18 depicts drain current vs. time for three different drain voltages.

In certain embodiments, biomechanical interaction on a gold coated cantilever is largely uniform across the surface with slight variation along its length. When the cantilever bends due to surface stress, an electronic readout chip may be placed at specific locations along the length of cantilever, so the strength of the surface stress across specific locations can be quantified. To measure such site-specific interactions between biomolecules, a cascade of BiMOS chips may be placed at specific locations on the cantilever. The BiMOS devices are placed in series, for example. In an embodiment, 3-5 transistors are separated by 5-10 micron. Readout electronics are passivated or protected from corrosion with an insulating silicon nitride layer for measuring a signal in biological fluids. Gold is coated on the cantilever in the final stage and is used for immobilizing receptors via alkane-thiol cross linkers, for example. Each of the transistors can be operated together or individually, for example. If the transistors are operated together, then a large current output can be accommodated, but it is difficult to determine where an intensity of the biomechanical interactions is higher. When the transistors are operated individually, an intensity of biomechanical interactions may be quantified at each location of the cantilever.

In certain embodiments, MOSFET-embedded microcantilevers for bio-chemical sensing and scanning probe microscopy applications may be designed in a variety of ways. In certain embodiments, geometry and orientation of embedded MOSFETs are modified to improve sensitivity of a sensor platform. Specifically, certain embodiments include embedded MOSFETs with a higher aspect ratio (width/length (W/L)) oriented with a MOSFET carrier transport direction parallel to the length of the microcantilever to help allow enhancing current sensitivity.

Figure 19:
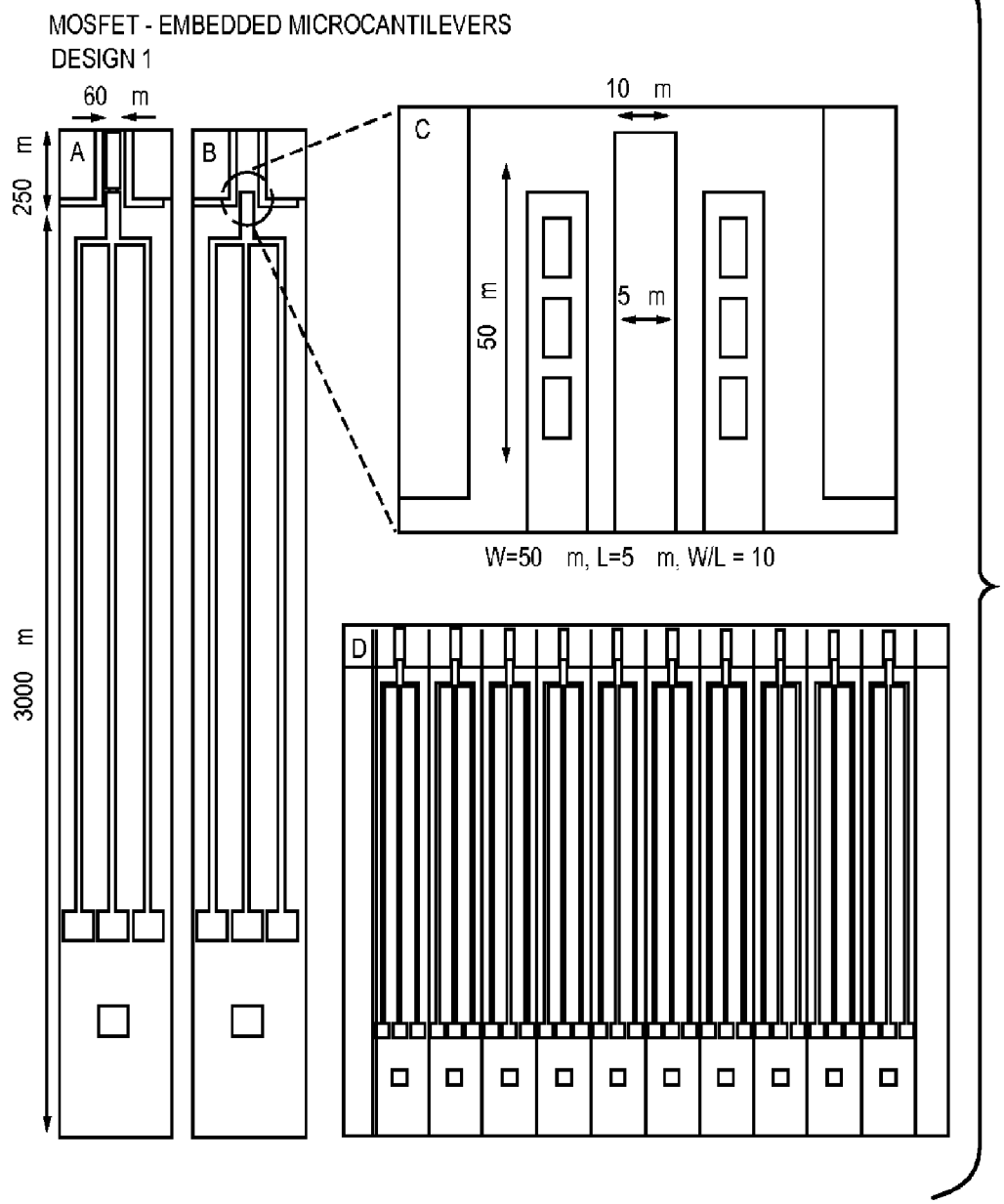
FIG. 19 illustrates an exemplary embodiment of a MOSFET-embedded microcantilever design.

FIGS. 19-24 illustrate several exemplary embodiments of a MOSFET-embedded microcantilever design for purposes of illustration only. A first MOSFET-embedded microcantilever design is shown in FIG. 19. For example, FIG. 19(A) shows a single cell of a gold-coated (sensing) microcantilever with an embedded MOSFET. FIG. 19(B) depicts a single cell of a $SiN_x$ (reference) microcantilever. FIG. 19(C) illustrates a magnified view of an embedded MOSFET with an aspect ratio of 10. The MOSFET carrier transport direction is perpendicular to the length of the cantilever. In FIG. 19(D) single cells, including 8 gold-coated (sensing) and 2 $SiN_x$ (reference) cantilevers, were combined to create a chip with a 10×1 array of microcantilevers.

Figure 20:
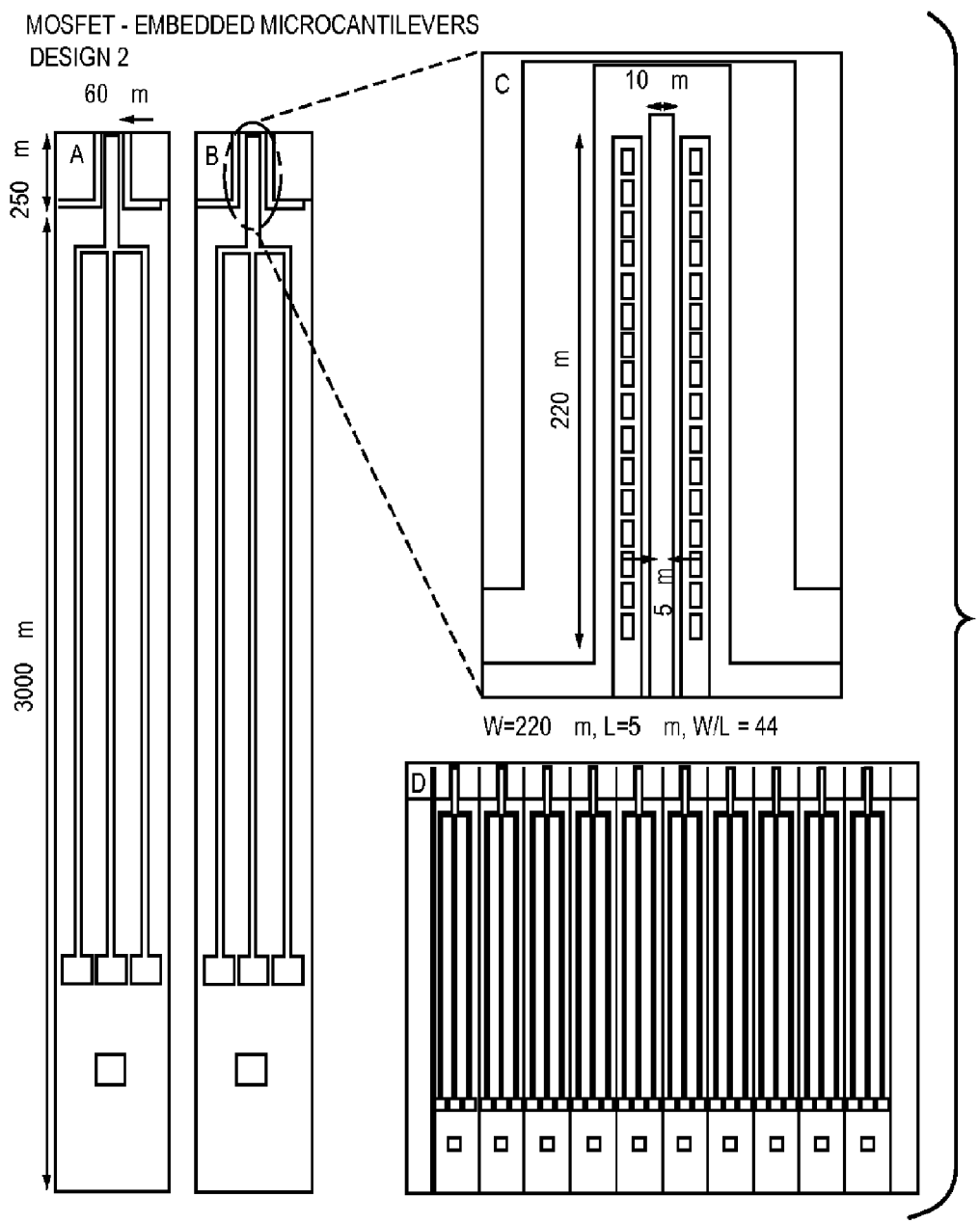
FIG. 20 illustrates an exemplary embodiment of a MOSFET-embedded microcantilever design.

A second MOSFET-embedded microcantilever design is shown in FIG. 20. FIG. 20(A) depicts a single cell of a gold-coated (sensing) microcantilever with an embedded MOSFET. FIG. 20(B) shows a single cell of a $SiN_x$ (reference) microcantilever. FIG. 20(C) shows a magnified view of an embedded MOSFET extended along the length of the cantilever, providing an aspect ratio of 44. The MOSFET carrier transport direction is perpendicular to the length of the cantilever. In FIG. 20(D), single cells, such as 8 gold-coated (sensing) and 2 $SiN_x$ (reference) cantilevers, were combined to create a chip with a 10×1 array of microcantilevers.

Figure 21:
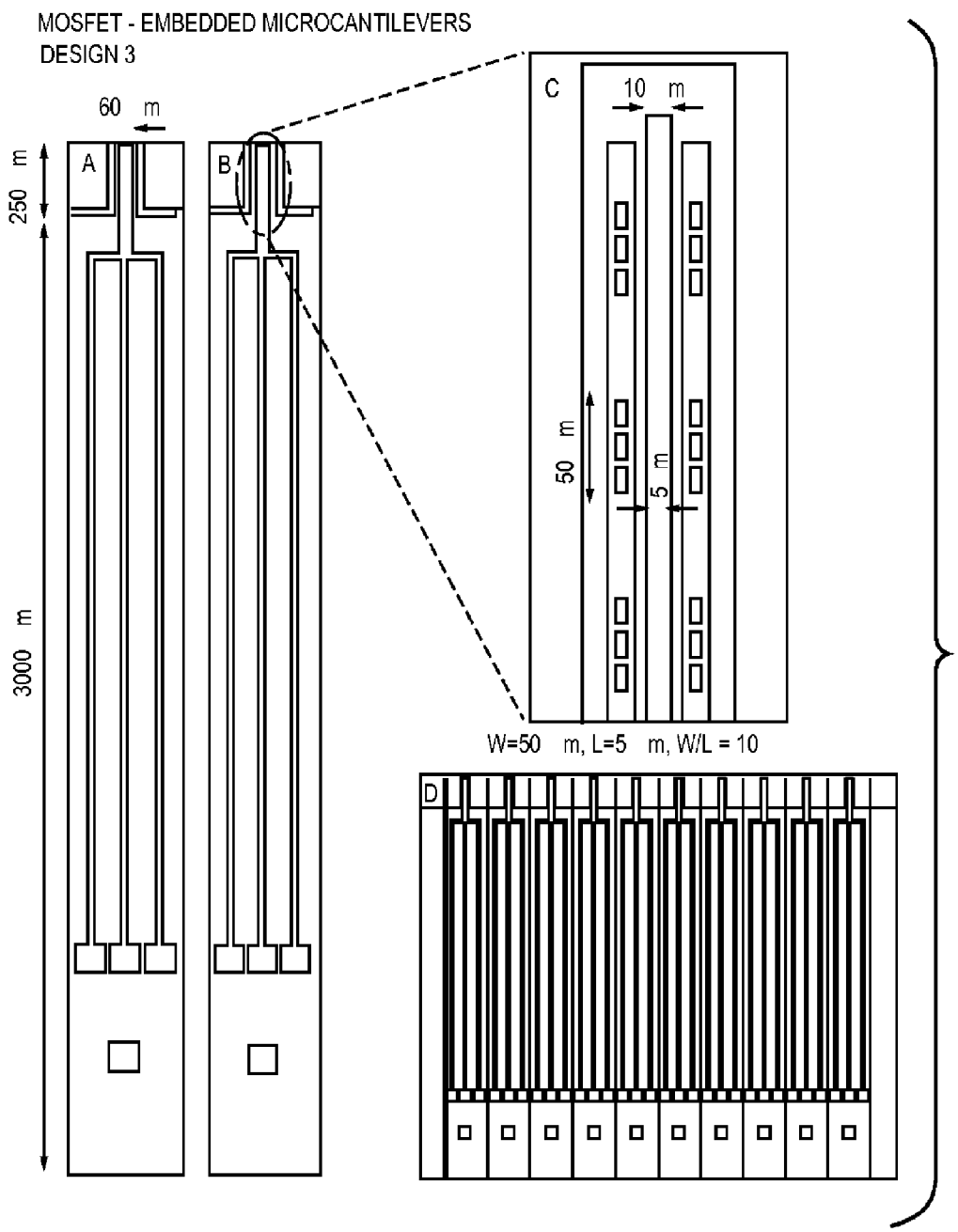
FIG. 21 illustrates an exemplary embodiment of a MOSFET-embedded microcantilever design.
Figure 22:
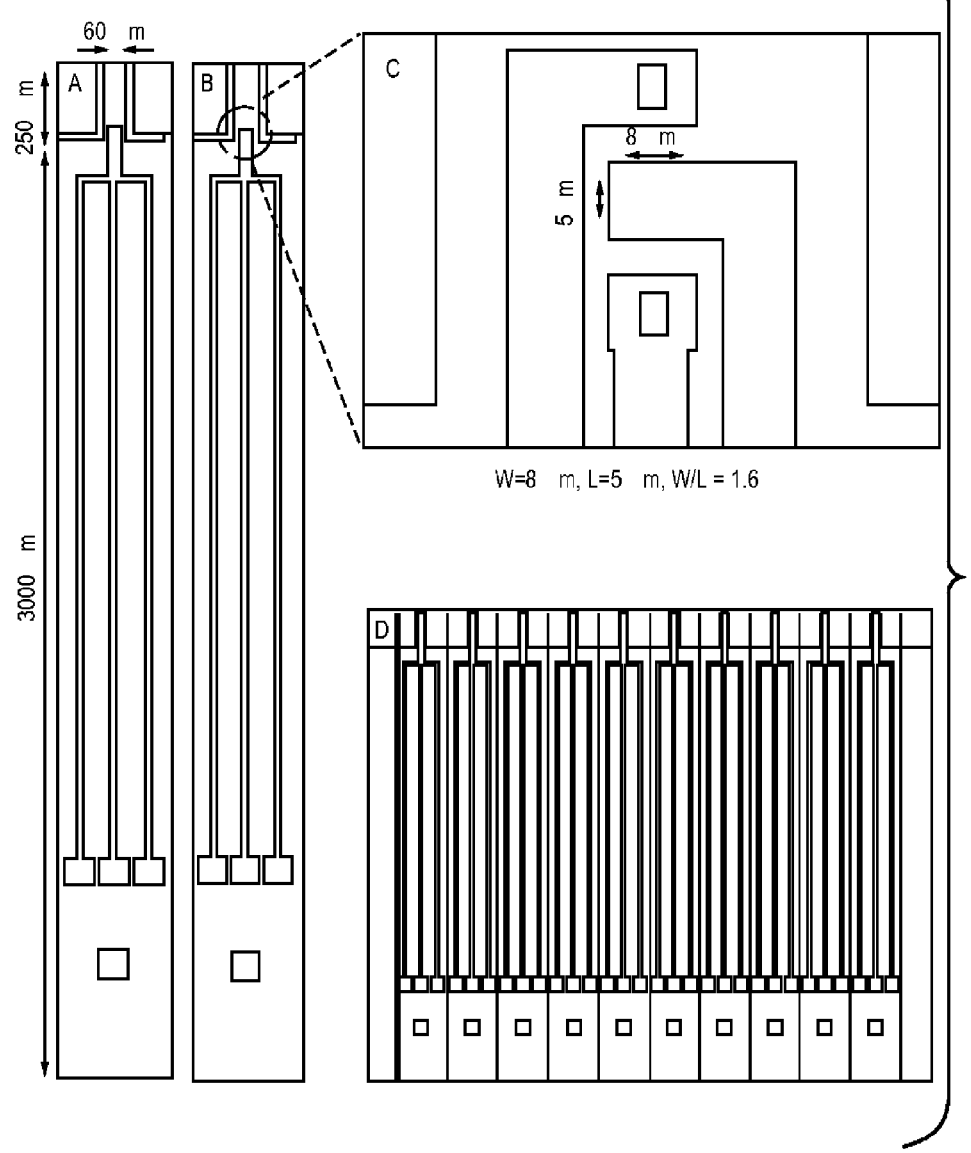
FIG. 22 illustrates an exemplary embodiment of a MOSFET-embedded microcantilever design.

A third MOSFET-embedded microcantilever design is shown in FIG. 21. FIG. 21(A) shows a single cell of a gold-coated (sensing) microcantilever with an embedded MOSFET. FIG. 21(B) shows a single cell of a $SiN_x$ (reference) microcantilever. FIG. 21(C) illustrates a magnified view of three embedded MOSFETs with an aspect ratio of 10. The MOSFET carrier transport direction is perpendicular to the length of the cantilever. In FIG. 21(D), single cells (e.g., 8 gold-coated (sensing) and 2 $SiN_x$ (reference) cantilevers) are combined to create a chip with a 10×1 array of microcantilevers.

In FIG. 22(A), a single cell of a gold-coated (sensing) microcantilever with an embedded MOSFET is shown. In FIG. 22(B), a single cell of a $SiN_x$ (reference) microcantilever is depicted. In FIG. 22(C), a magnified view of an embedded MOSFET with an aspect ratio of 1.6 is illustrated. The MOSFET carrier transport direction is parallel to the length of the cantilever. FIG. 22(D) shows a combination of single cells, 8 gold-coated (sensing) and 2 $SiN_x$ (reference) cantilevers, that were combined to create a chip with a 10×1 array of microcantilevers.

Figure 23:
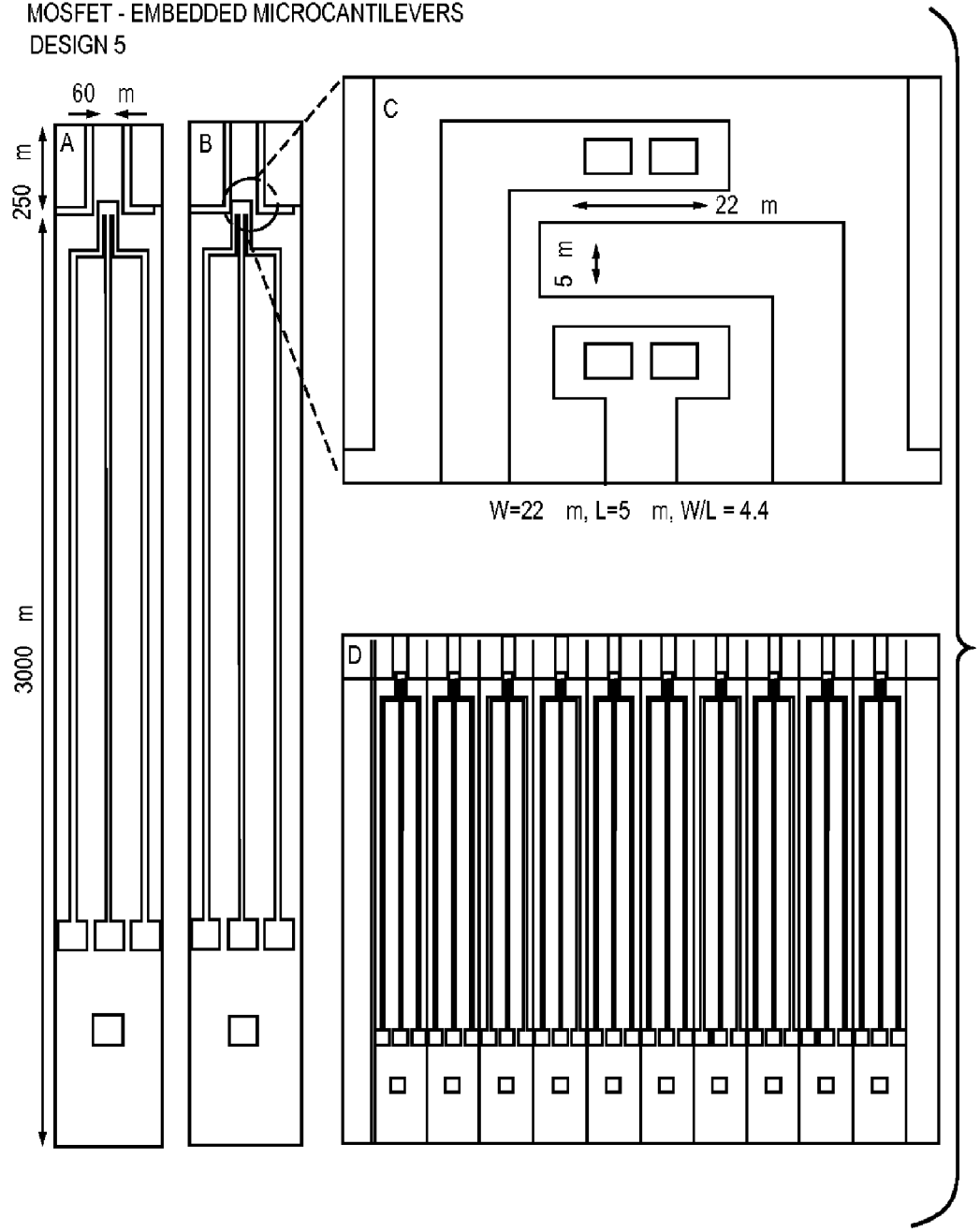
FIG. 23 illustrates an exemplary embodiment of a MOSFET-embedded microcantilever design.

FIG. 23 depicts a fifth design for a MOSFET-embedded microcantilever. In FIG. 23(A), a single cell of an 80 μm-wide gold-coated (sensing) microcantilever with an embedded MOSFET is shown. FIG. 23(B) shows a single cell of a $SiN_x$ (reference) microcantilever. FIG. 23(C) illustrates a magnified view of an embedded MOSFET with an aspect ratio of 4.4. The MOSFET carrier transport direction is parallel to the length of the cantilever. In FIG. 23(D), single cells, such as 8 gold-coated (sensing) and 2 $SiN_x$ (reference) cantilevers, are combined to create a chip with a 10×1 array of microcantilevers.

Figure 24:
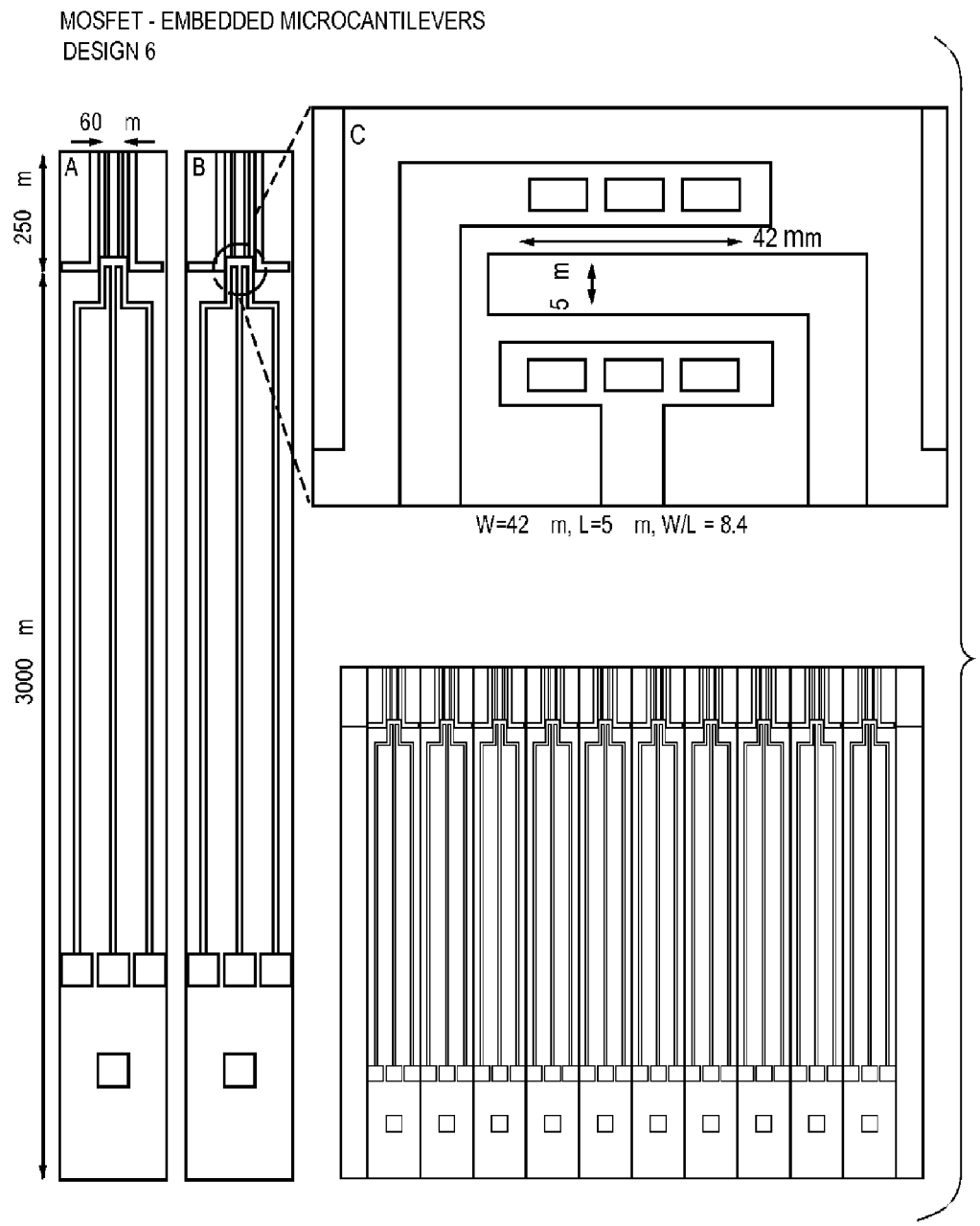
FIG. 24 illustrates an exemplary embodiment of a MOSFET-embedded microcantilever design.

In FIG. 24, a sixth design for a MOSFET-embedded microcantilever is illustrated. FIG. 24(A) shows a single cell of a 100 μm-wide gold-coated (sensing) microcantilever with an embedded MOSFET. FIG. 24(B) shows a single cell of a $SiN_x$ (reference) microcantilever. FIG. 24(C) depicts a magnified view of an embedded MOSFET with an aspect ratio of 8.4. The MOSFET carrier transport direction is parallel to the length of the cantilever. In FIG. 24(D), single cells, such as 8 gold-coated (sensing) and 2 $SiN_x$ (reference) cantilevers, are combined to create a chip with a 10×1 array of microcantilevers.

Certain embodiments provide electronic detection of bio-chemical interactions using embedded BiMOS technology. In certain embodiments, integrated, embedded BiMOS transistors are fabricated with electronic readouts and built-in background filters on a high stress region of a cantilever. Cantilever fabrication may employ SOI (silicon on insulator) wafers with buried oxide etch-stop layers, which allow probes to be realized with a fully encapsulated BiMOS transistor.

In certain embodiments, a cantilever may include a cascaded MOSFET-embedded microcantilever with top finger electrodes for bio-chemical sensing and scanning probe microscopy applications. In such a microcantilever design, geometry (e.g., an aspect ratio (W/L)) of the embedded MOSFETs is modified to have a larger drain current. Higher drain current allows detection of cantilever deflection down to sub-nanometer range.

Additionally, cascaded MOSFETs may be oriented to have carrier transport in a direction parallel or perpendicular to the length of the cantilever. Stress in the cantilever is typically non-uniform and differential in nature. Thus, stress in the cantilever can result in a differential change in carrier mobility in a MOSFET channel, which can be used as a basis for enhanced sensitivity.

If measured at different locations along the length of a cantilever, a response pattern for each test analyte (e.g., a substance under test or analysis) can be generated from non-uniform and differential stress due to cantilever bending. In certain embodiments, MOSFETs are embedded in a cantilever at different locations with all source and gate terminals shorted together but with separate drains to provide a stress-induced differential response. Measurement of stress due to cantilever bending from cascaded MOSFETs, if summed together, can be used to increase a sensitivity manifold, for example.

In certain embodiments, cantilevers are patterned with top interdigitated or interwoven electrodes. Measurement of electrical response across the interdigitated electrodes together with mechanical response may be measured as a change in MOSFET drain current to help improve reliability.

FIGS. 25-33 illustrate an exemplary design process for a cascaded MOSFET-embedded multi-input microcantilever. In FIG. 25, a source and drain implementation window is added for a MOSFET. FIG. 25(A) illustrates a single cell of a $SiN_x$ (reference) microcantilever 2510. In FIG. 25(B), a single cell of a gold-coated (sense) microcantilever 2520 is shown. FIG. 25(C) depicts a magnified view of cascaded MOSFETs 2530. The MOSFETs carrier transport direction is perpendicular to the length of the cantilever. In FIG. 25(D), single cells, such as 8 gold-coated (sense) and 2 $SiN_x$ (reference) cantilevers, are combined to create a chip with a 10×1 array of microcantilevers 2540.

FIG. 26 shows a dielectric layer for a cascaded MOSFET-embedded multi-input cantilever. In FIG. 26(A), a single cell of a $SiN_x$ (reference) microcantilever is illustrated. In FIG. 26(B), a single cell of a gold-coated (sense) microcantilever is shown. FIG. 26(C) depicts a magnified view of cascaded MOSFETs. The MOSFETs carrier transport direction is perpendicular to the length of the cantilever. In FIG. 26(D), single cells, such as 8 gold-coated (sense) and 2 $SiN_x$ (reference) cantilevers, are combined to create a chip with a 10×1 array of microcantilevers.

Figure 27:
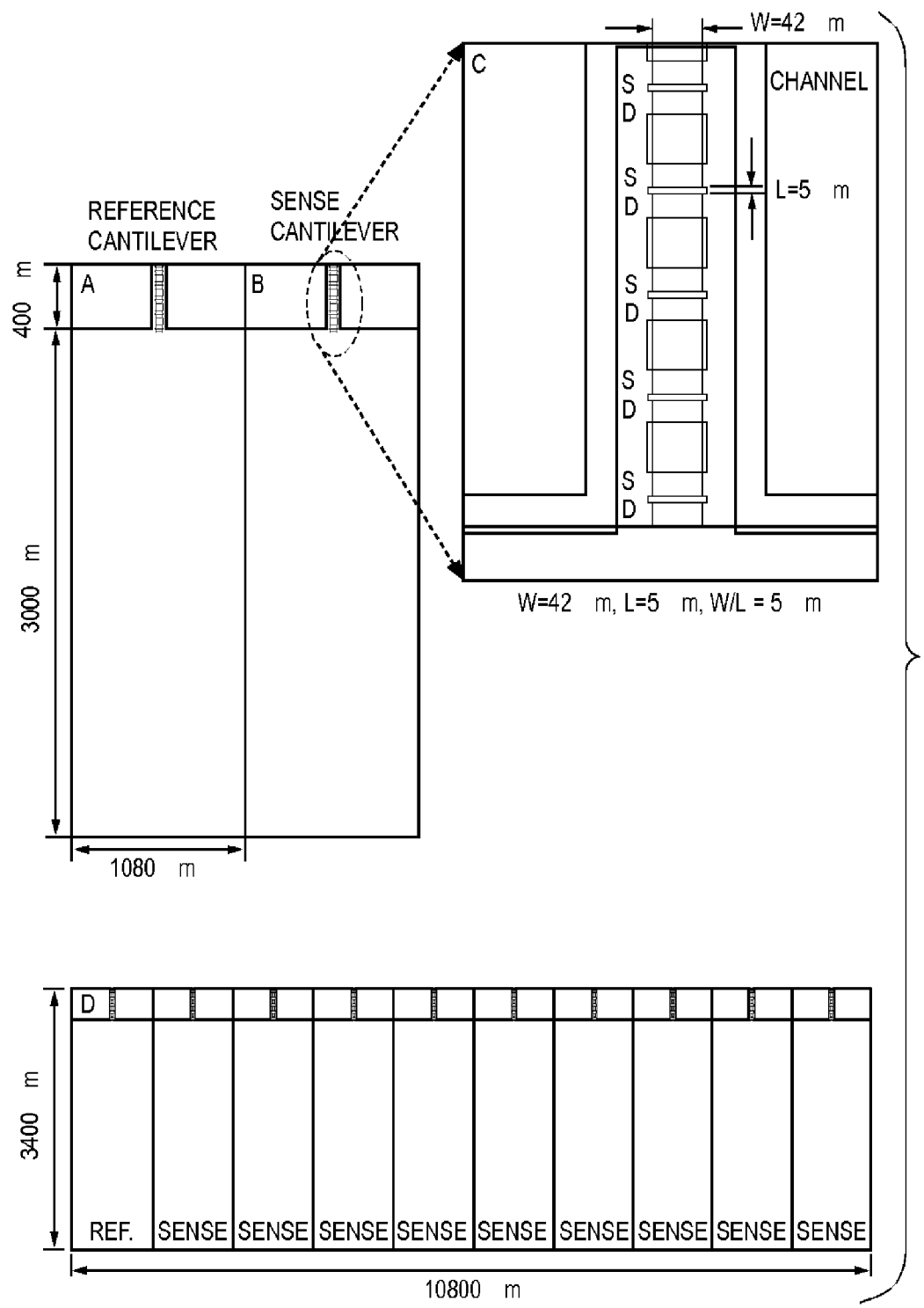
FIG. 27 illustrates an exemplary design process for a cascaded MOSFET-embedded multi-input microcantilever.

FIG. 27 illustrates source and drain contact openings for a cascaded MOSFET-embedded multi-input cantilever. FIG. 27(A) shows a single cell of a $SiN_x$ (reference) microcantilever. FIG. 27(B) shows a single cell of a gold-coated (sense) microcantilever. FIG. 27(C) illustrates a magnified view of cascaded MOSFETs. The MOSFET carrier transport direction is perpendicular to the length of the cantilever. As shown in FIG. 27(D), single cells, including 8 gold-coated (sense) and 2 $SiN_x$ (reference) microcantilevers, may be combined to form a chip with a 10×1 array of microcantilevers.

Figure 28:
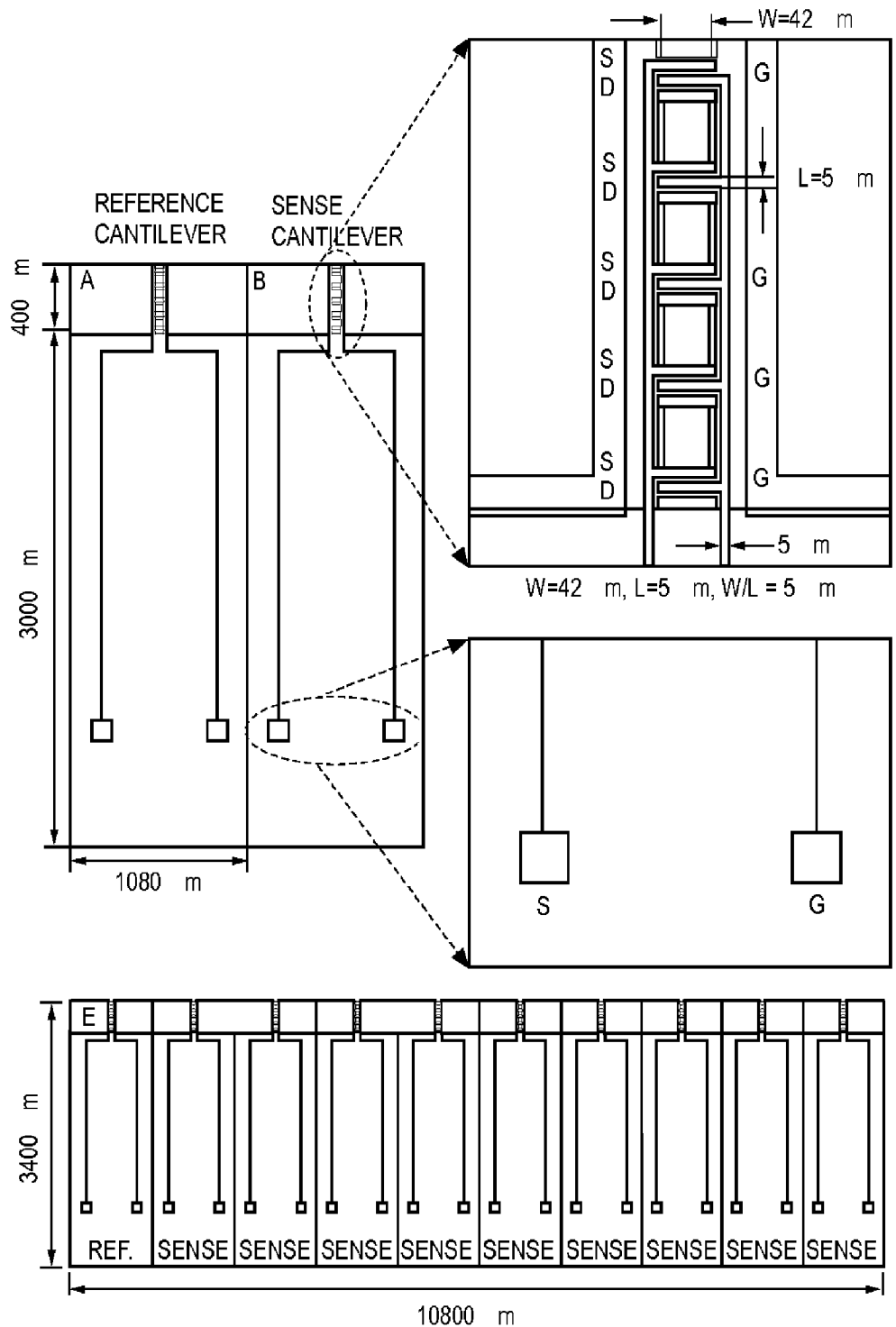
FIG. 28 illustrates an exemplary design process for a cascaded MOSFET-embedded multi-input microcantilever.

FIG. 28 illustrates metal deposition for source, drain and gate contacts in a cascaded MOSFET-embedded multi-input microcantilever. In FIG. 28, drains and sources are shorted together. FIG. 28(A) shows a single cell of a $SiN_x$ (reference) microcantilever. FIG. 28(B) shows a single cell of a gold-coated (sense) microcantilever. FIG. 28(C) illustrates a magnified view of cascaded MOSFETs. The MOSFET carrier transport direction is perpendicular to the length of the cantilever. FIG. 28(D) shows a magnified view of contact pads. As shown in FIG. 28(E), single cells, including 8 gold-coated (sense) and 2 $SiN_x$ (reference) microcantilevers, may be combined to form a chip with a 10×1 array of microcantilevers.

Figure 29:
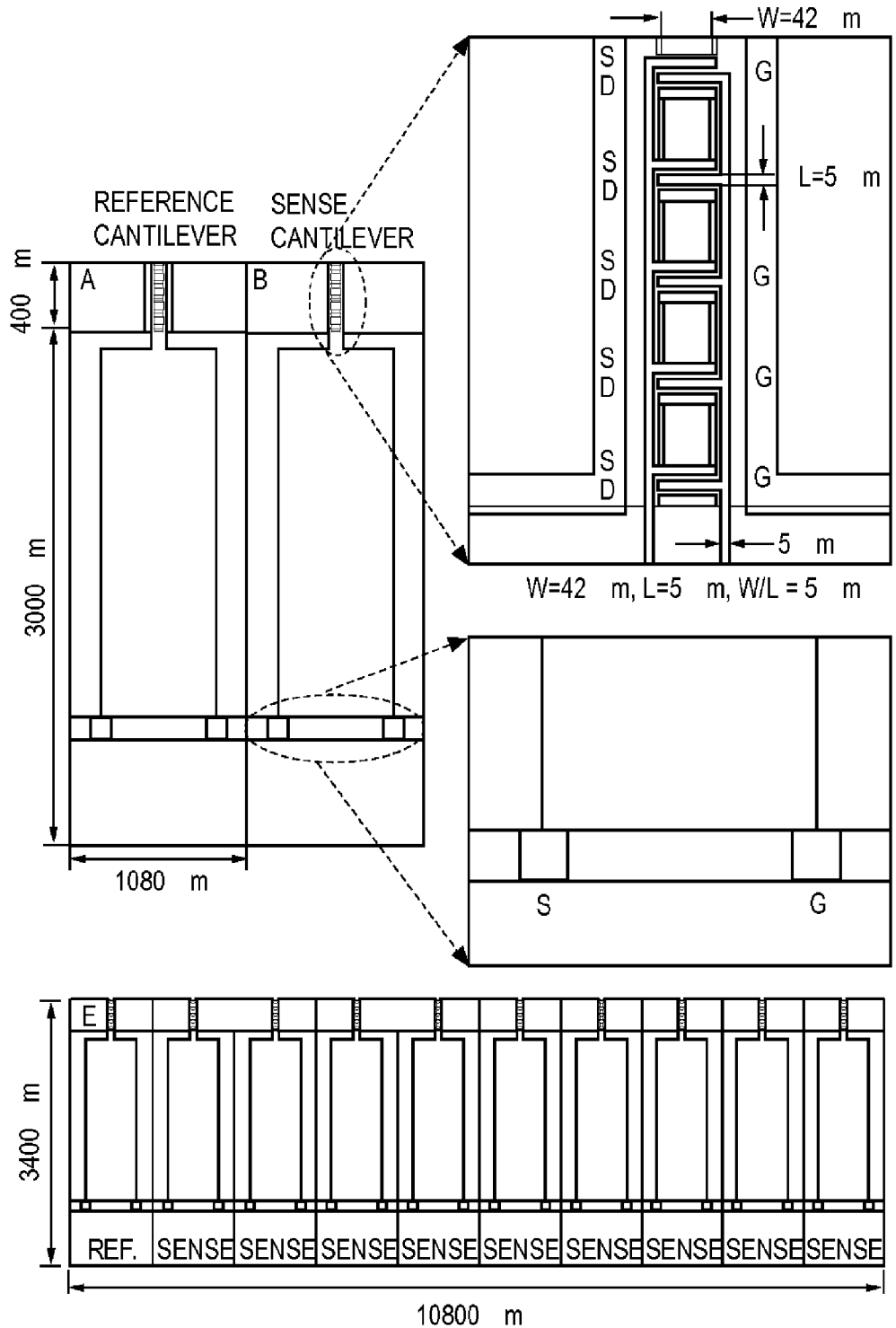
FIG. 29 illustrates an exemplary design process for a cascaded MOSFET-embedded multi-input microcantilever.

FIG. 29 shows a cascaded MOSFET-embedded multi-input microcantilever with a deposited nitrate layer having openings for drain contacts. In FIG. 29, there are two different openings for source and gate pads. FIG. 29(A) shows a single cell of a $SiN_x$ (reference) microcantilever. FIG. 29(B) shows a single cell of a gold-coated (sense) microcantilever. FIG. 29(C) illustrates a magnified view of cascaded MOSFETs. The MOSFET carrier transport direction is perpendicular to the length of the cantilever. FIG. 29(D) shows a magnified view of contact pads. As shown in FIG. 29(E), single cells, including 8 gold-coated (sense) and 2 $SiN_x$ (reference) microcantilevers, may be combined to form a chip with a 10×1 array of microcantilevers.

Figure 30:
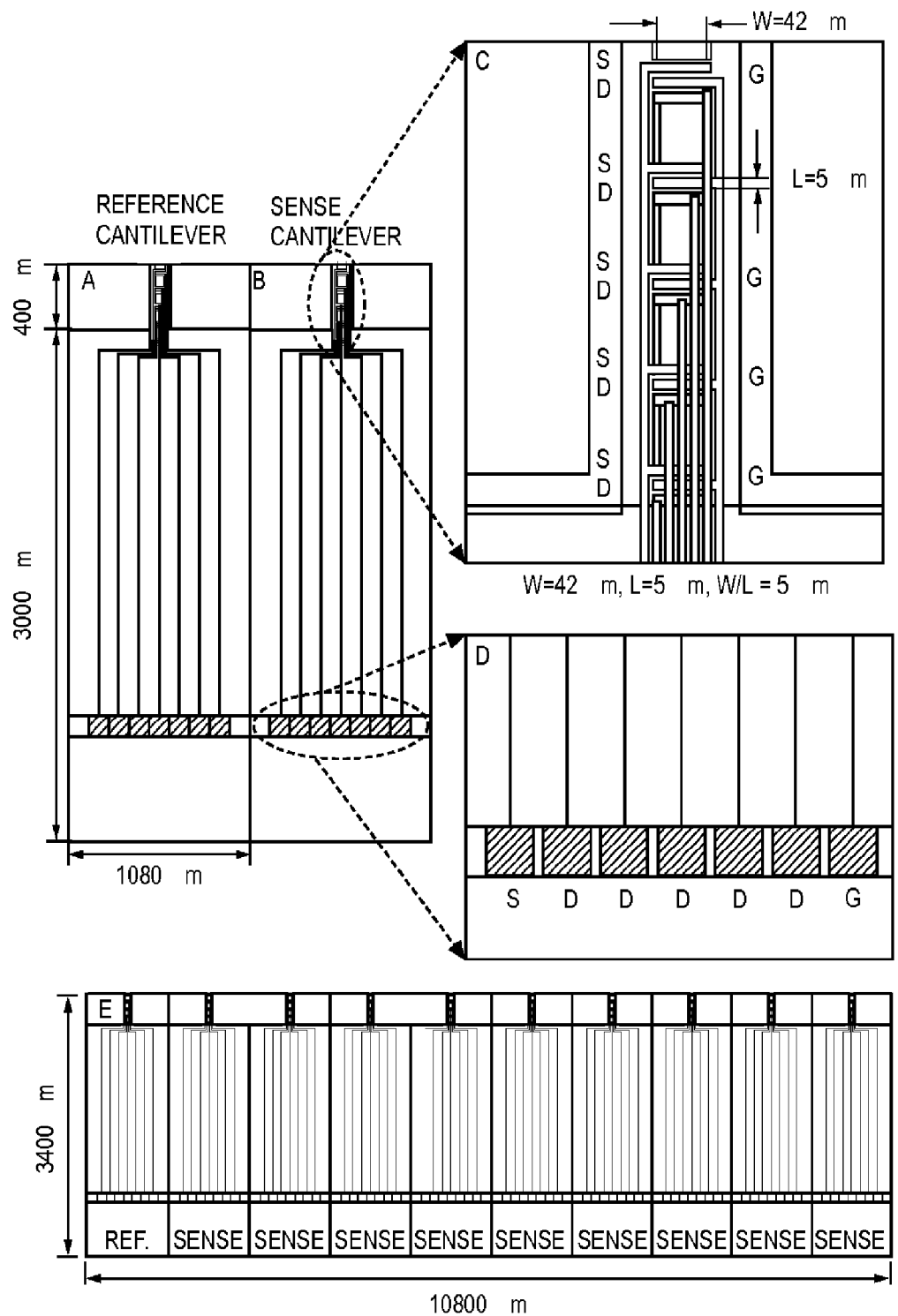
FIG. 30 illustrates an exemplary design process for a cascaded MOSFET-embedded multi-input microcantilever.

FIG. 30 shows a cascaded MOSFET-embedded multi-input microcantilever having metal contacts to drains. FIG. 30(A) shows a single cell of a $SiN_x$ (reference) microcantilever. FIG. 30(B) shows a single cell of a gold-coated (sense) microcantilever. FIG. 30(C) illustrates a magnified view of cascaded MOSFETs. The MOSFET carrier transport direction is perpendicular to the length of the cantilever. FIG. 30(D) shows a magnified view of contact pads. As shown in FIG. 30(E), single cells, including 8 gold-coated (sense) and 2 $SiN_x$ (reference) microcantilevers, may be combined to form a chip with a 10×1 array of microcantilevers.

Figure 31:
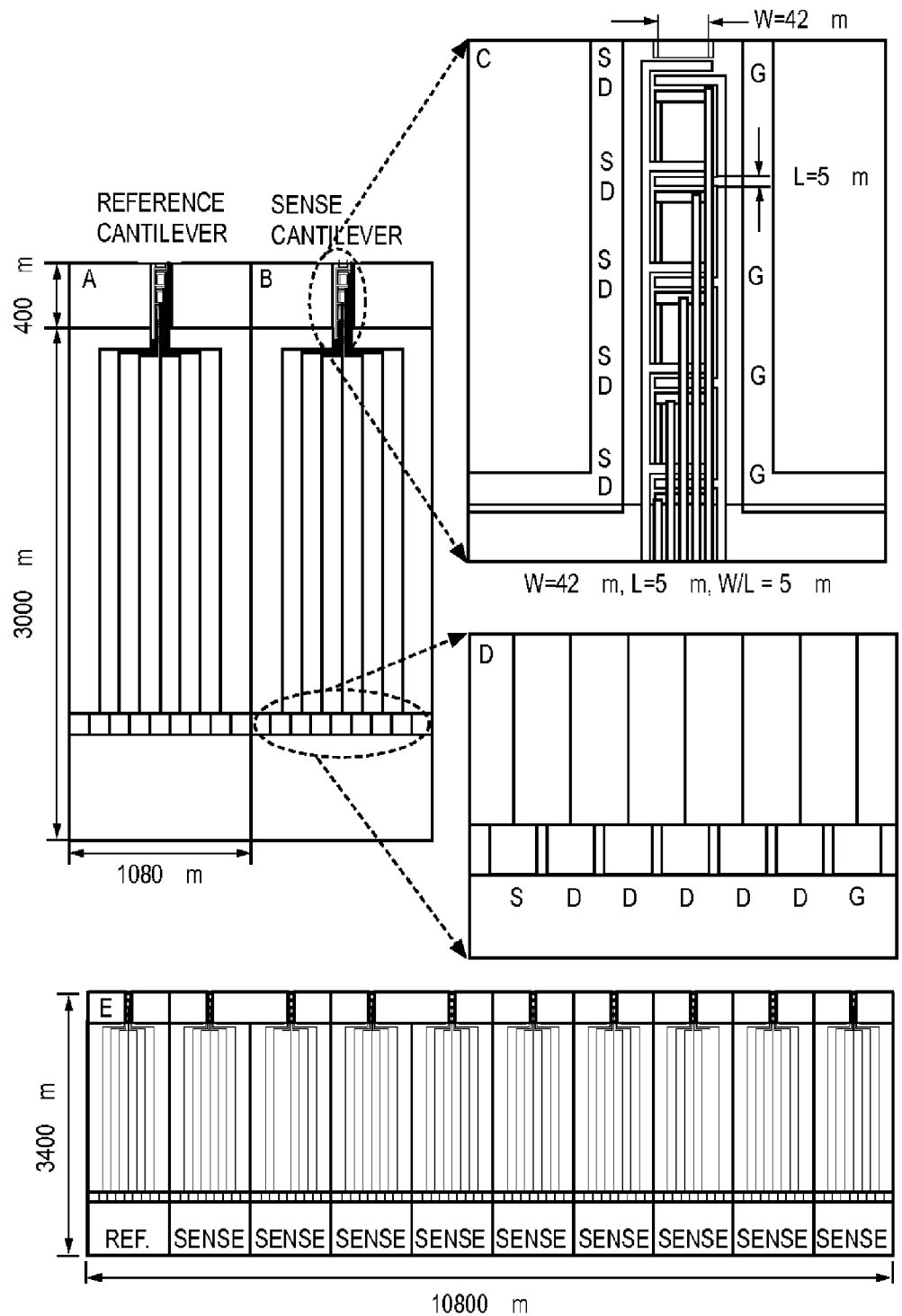
FIG. 31 illustrates an exemplary design process for a cascaded MOSFET-embedded multi-input microcantilever.

FIG. 31 shows a cascaded MOSFET-embedded multi-input microcantilever with a nitride layer having openings for source and drain pads. FIG. 31(A) shows a single cell of a $SiN_x$ (reference) microcantilever. FIG. 31(B) shows a single cell of a gold-coated (sense) microcantilever. FIG. 31(C) illustrates a magnified view of cascaded MOSFETs. The MOSFET carrier transport direction is perpendicular to the length of the cantilever. FIG. 31(D) shows a magnified view of contact pads. As shown in FIG. 31(E), single cells, including 8 gold-coated (sense) and 2 $SiN_x$ (reference) microcantilevers, may be combined to form a chip with a 10×1 array of microcantilevers.

Figure 32:
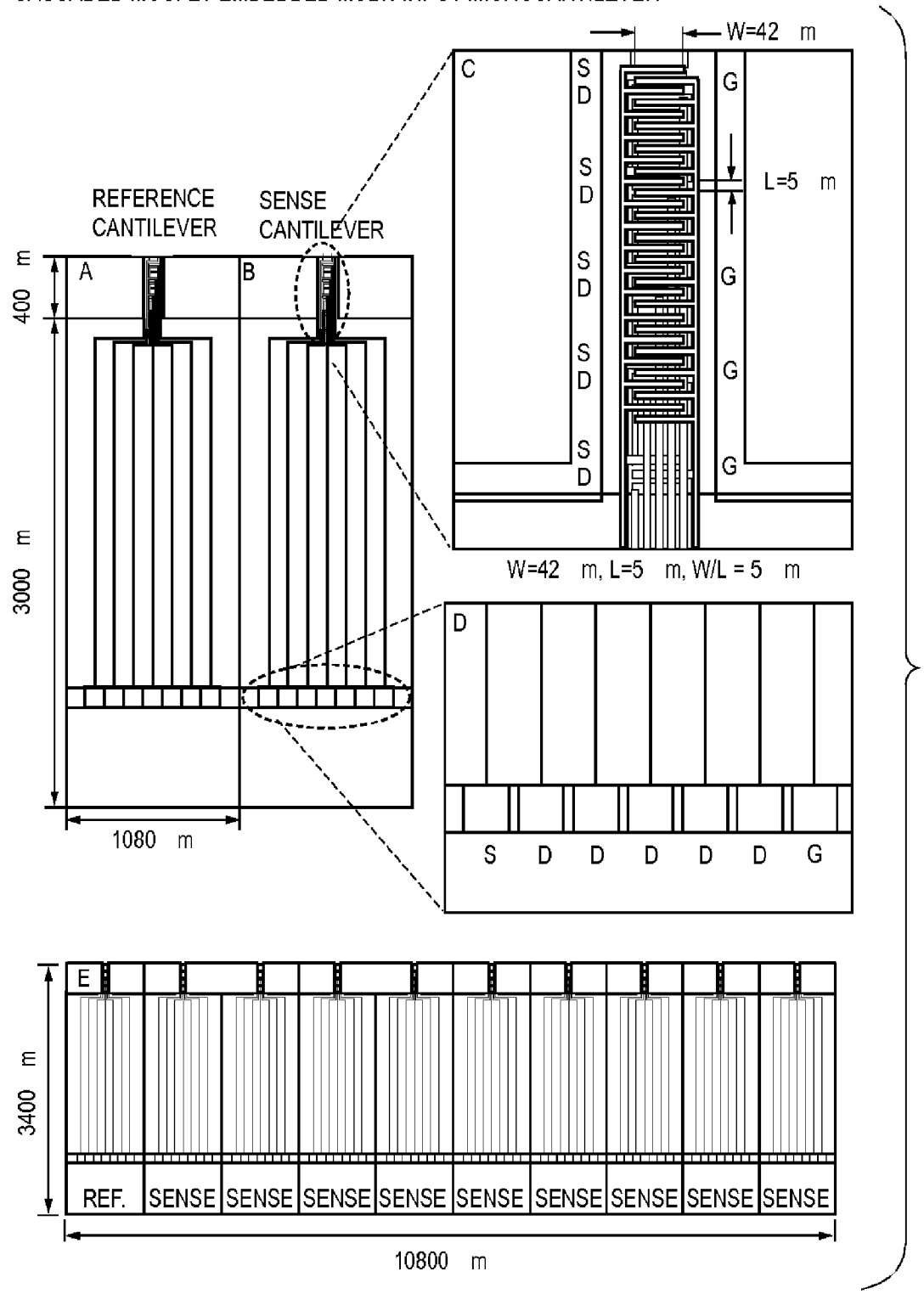
FIG. 32 illustrates an exemplary design process for a cascaded MOSFET-embedded multi-input microcantilever.

FIG. 32 shows a cascaded MOSFET-embedded multi-input microcantilever with deposition of finger electrodes. FIG. 32(A) shows a single cell of a $SiN_x$ (reference) microcantilever. FIG. 32(B) shows a single cell of a gold-coated (sense) microcantilever. FIG. 32(C) illustrates a magnified view of cascaded MOSFETs. The MOSFET carrier transport direction is perpendicular to the length of the cantilever. FIG. 32(D) shows a magnified view of contact pads. As shown in FIG. 32(E), single cells, including 8 gold-coated (sense) and 2 $SiN_x$ (reference) microcantilevers, may be combined to form a chip with a 10×1 array of microcantilevers.

Figure 33:
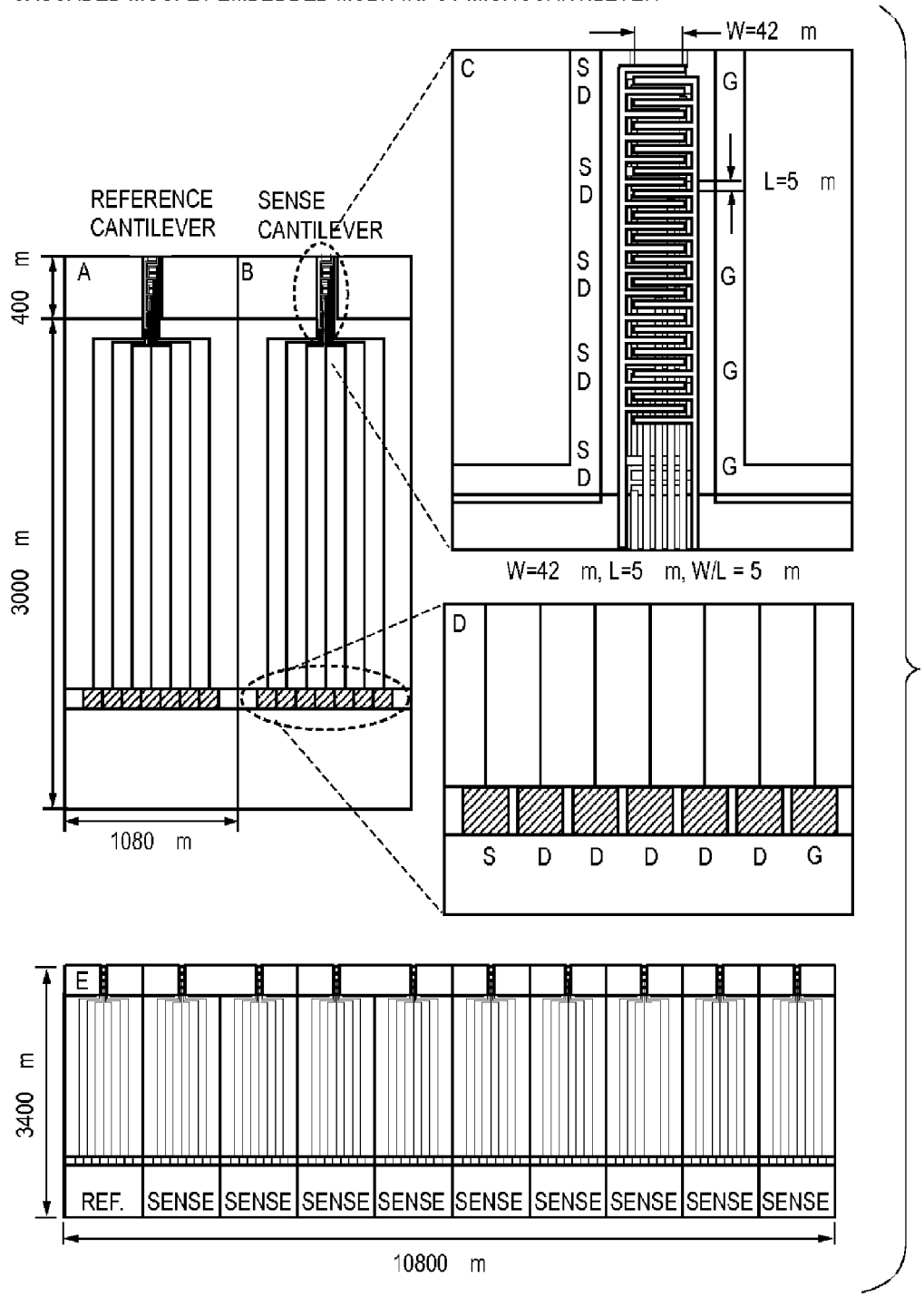
FIG. 33 illustrates an exemplary design process for a cascaded MOSFET-embedded multi-input microcantilever.

FIG. 33 shows a cascaded MOSFET-embedded multi-input microcantilever with a passivation layer added. FIG. 33(A) shows a single cell of a $SiN_x$ (reference) microcantilever. FIG. 33(B) shows a single cell of a gold-coated (sense) microcantilever. FIG. 33(C) illustrates a magnified view of cascaded MOSFETs. The MOSFET carrier transport direction is perpendicular to the length of the cantilever. FIG. 33(D) shows a magnified view of contact pads. As shown in FIG. 33(E), single cells, including 8 gold-coated (sense) and 2 $SiN_x$ (reference) microcantilevers, may be combined to form a chip with a 10×1 array of microcantilevers.

Figure 34:
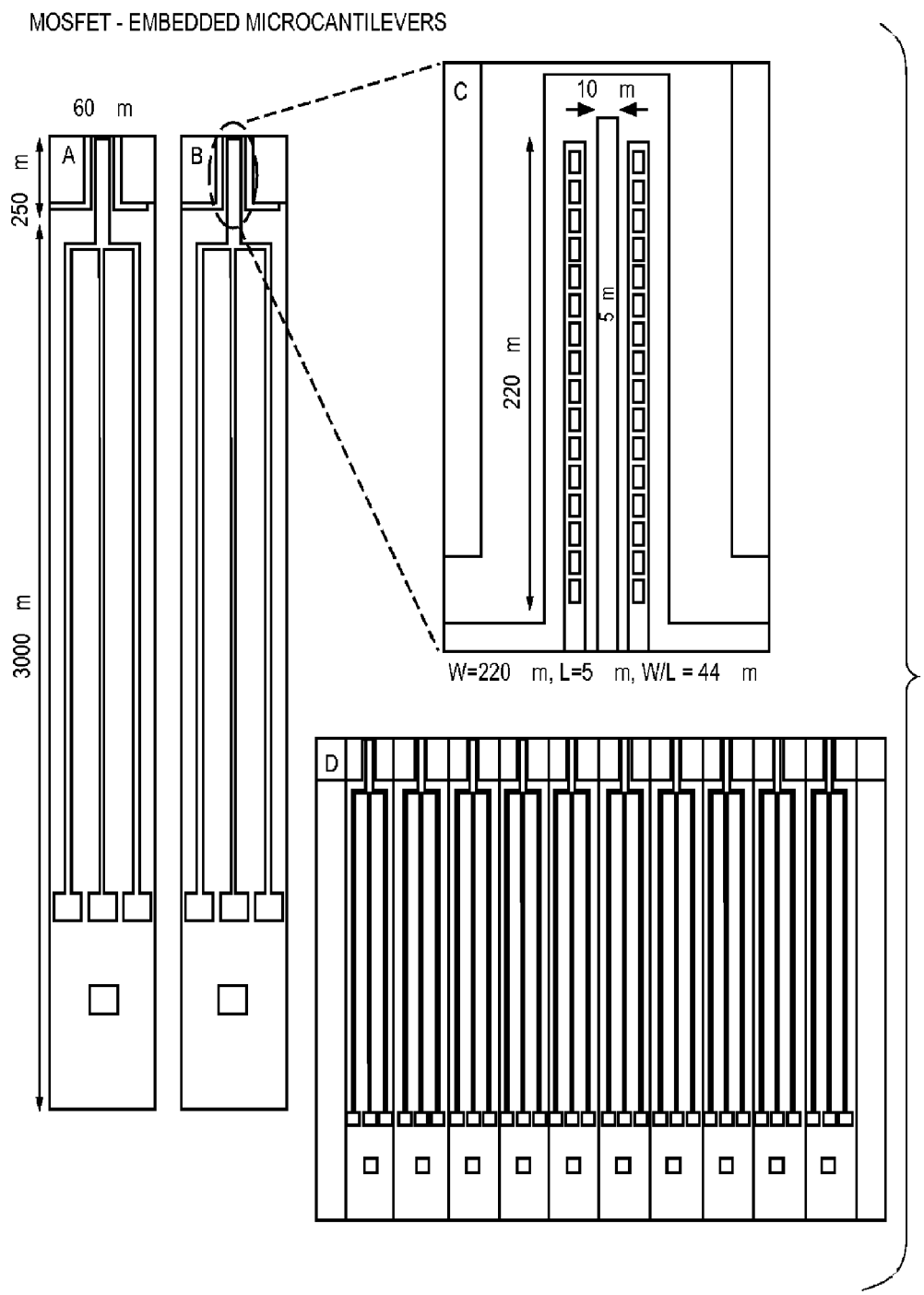
FIG. 34 shows a schematic of cascaded embedded MOSFET transistors across a length of a cantilever.

As another example, FIG. 34 shows a detailed schematic of cascaded embedded MOSFET transistors across a length of a cantilever. In this configuration, current flows perpendicular to the cantilever length. The embedded-MOSFET transistor is positioned across the length of the cantilever. This positioning not only gives high current output but also measures biomechanics across the length of the cantilever. The various layers used in fabricating this cascaded embedded MOSFET-based electronic readout are as follows: 1) Layer 1: Deposition of field oxide up to 0.4 μm in thickness for device and contact isolations; 2) Layer 2: Window opening for source and drain implementation; 3) Layer 3: Cantilever definition and base; 4) Layer 4: Contact opening for metallization; 5) Layer 5: Contact lithography for metal deposition for source, drain and gate; 6) Layer 6: Passivation layer over the entire cantilever to protect the MOSFET from shorting in liquids; 7) Layer 7: Gold deposition for biomolecular recognition; and 8) Layer 8: Final etching from back side to release the cantilever.

Figure 35:
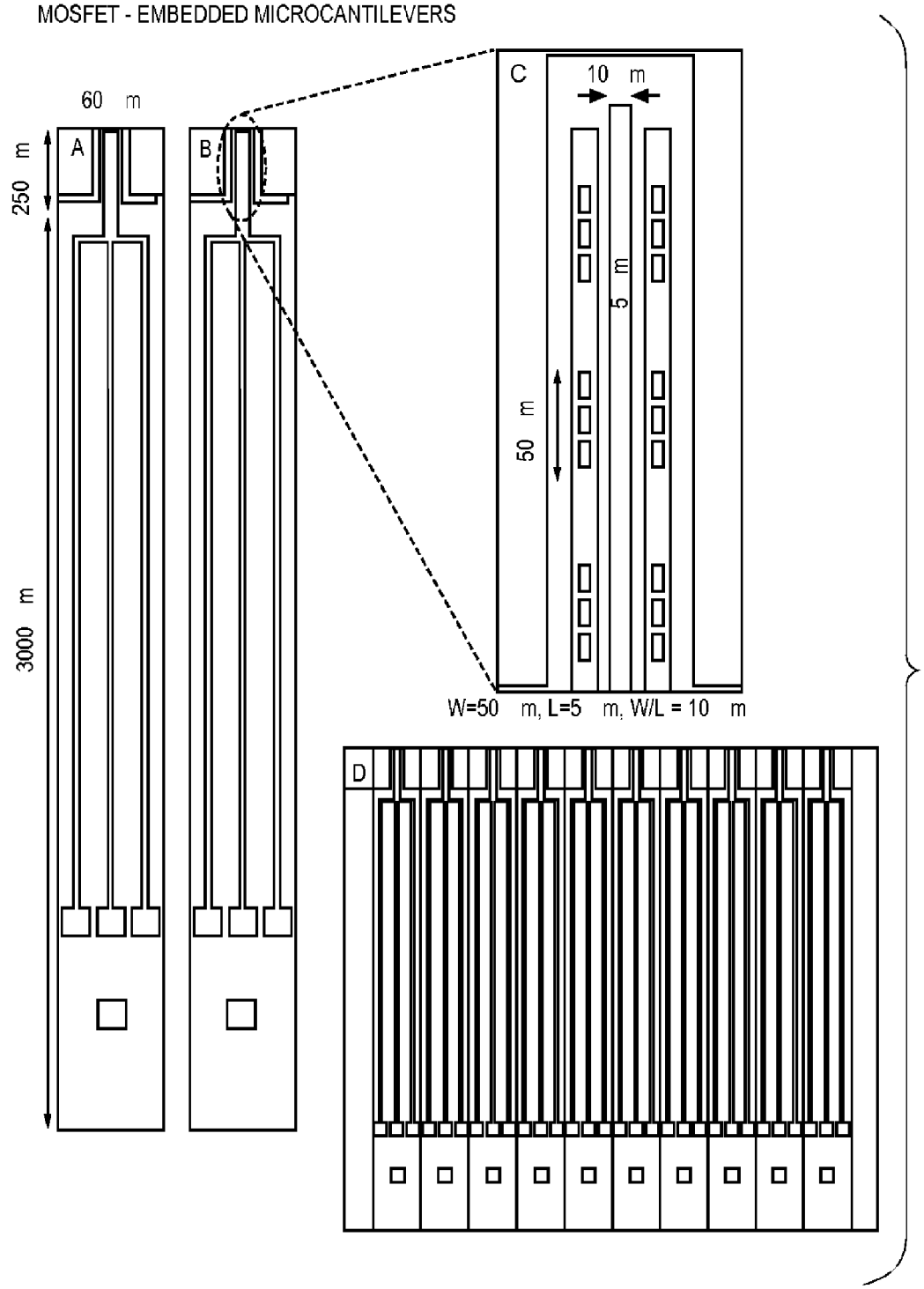
FIG. 35 shows cascaded MOSFET transistors isolated from each other by 5-10 micron spacing.

FIG. 35 shows cascaded MOSFET transistors isolated from each other by 5-10 micron spacing. Such design will help to quantify the biomechanics at each specific location of the cantilever. Transistors can be controlled individually. The layer specifications of FIG. 35 are the same as in FIG. 34.

Figure 36:
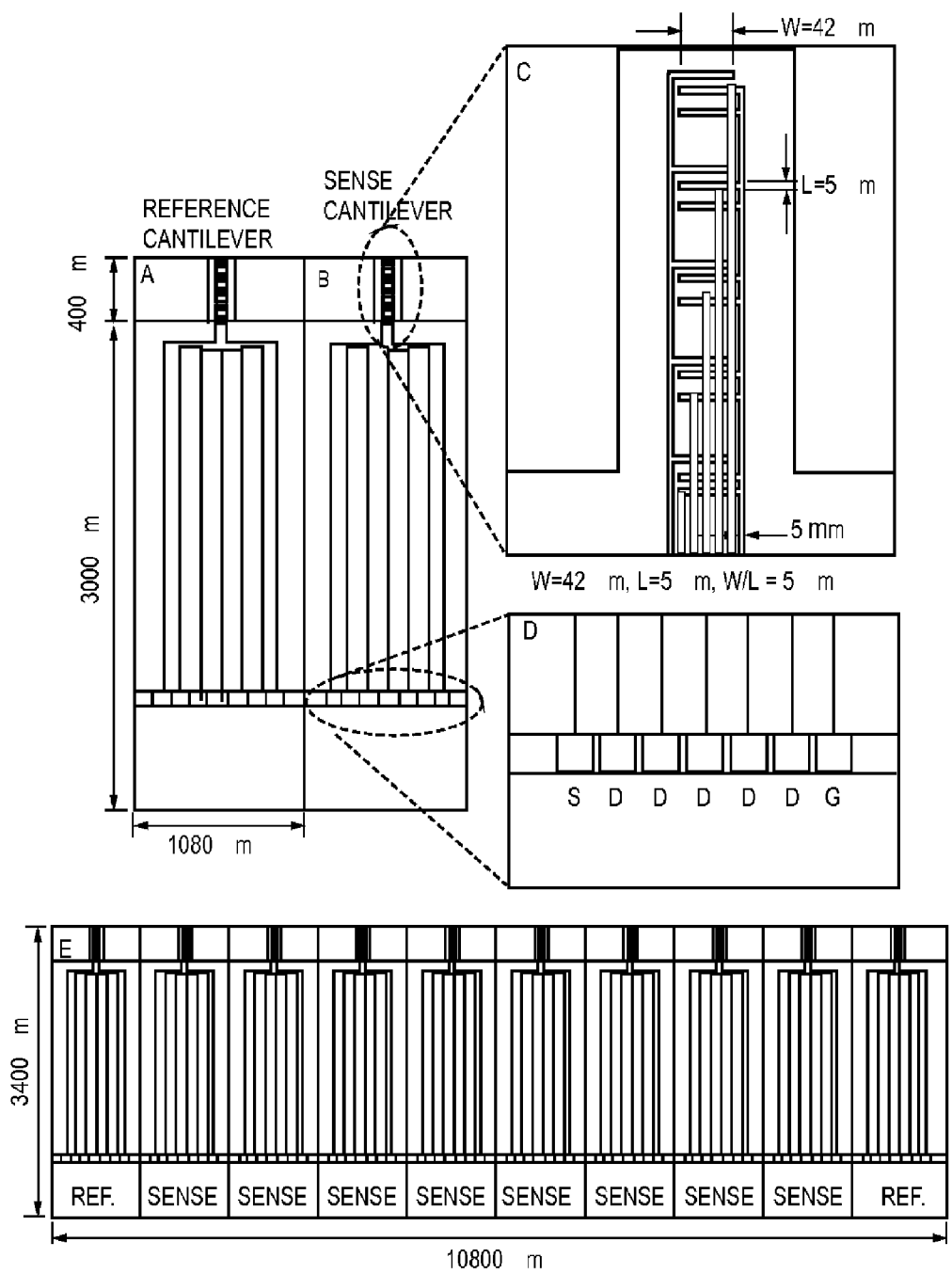
FIG. 36 shows a cascaded MOSFET transistor across the entire length of a cantilever and individually separated.

FIG. 36 shows a cascaded MOSFET transistor across the entire length of a cantilever and individually separated. Here, current flows along the length of the cantilever. Since the longitudinal stress is more as compared to transverse stress, this design should significantly enhance drain current sensitivity of embedded MOSFET transistors. Additionally, individual cascaded embedded MOSFET transistors will quantify the biomolecular interaction, and the detection level can go down to few molecular interactions. FIG. 36 also shows the details of individual layers. For example, FIG. 36 includes 1) Layer 1: Field oxide (e.g., 04. μm thick); 2) Layer 2: Windows for source and drain implementation; 3) Layer 3: Cantilever definition; 4) Layer 4: Contact holes for source and gate contacts only; 5) Layer 5: Contact lithography for source, drain and gate, which is followed by metallization over source and gate; 6) Layer 6: Passivation layer; 7) Layer 7: Contact lithography for drain contacts; 8) Layer 8: Metallization for drain; 9) Layer 9: Passivation of cascaded MOSFETs; and 10) Layer 10: Gold deposition for biomolecular recognition.

In certain embodiments, an electronic transduction paradigm includes two-dimensional microcantilever arrays with geometrically configured Bi-MOSFETs (metal-oxide semiconductor field-effect transistors) embedded in a high stress region of one or more microcantilevers, optimized or improved after finite-element analysis simulations. Deflection of the microcantilever induced by specific bio-chemical binding events leads to a precise measurable and reproducible change in the drain current of the MOSFET buried in the microcantilevers, thereby providing a new label- and optics-free, all-electronic signal transduction mechanism with increased sensitivity.

A BiMOS detection method offers a number of advantages over traditional piezoresistive or capacitive sensor elements because of, among other things, small size, high sensitivity, and simple direct current measurement compared to the complex piezoresistive measurements, as well as compatibility with direct monolithic integration with application-specific integrated circuits. Additionally, small channel lengths of MOSFET devices provide more localized stress measurements. BiMOS-embedded microcantilever detection allows for massively parallel on-chip signal sensing, multiplexing and remote-addressability via on-chip integrating of RF (Radio Frequency) elements as well as photovoltaics for local power supply.

Use of an Insulated-Gate Field-Effect Transistor (IGFET)-based force cantilever sensor has been reported for scanning probe microscopy applications only (e.g., Shivram, U.S. Pat. No. 6,237,399. Among many other things, Shivram does not disclose a BiMOS embedded in a cantilever structure wherein the BiMOS includes a metal-oxide semiconductor field effect transistor measuring deflection of the cantilever and a bipolar transistor providing an amplified signal. Nor does Shivram disclose a piezo-actuator on or embedded in the cantilever structure to provide bending of the cantilever structure or a feedback circuit responsive to the signal from the BiMOS to control the piezo-actuator. The force sensitivity reported for scanning probe microscopy has not been configured for high sensitivity for small changes in the drain current of a FET and is not applicable to Bio-Chemical sensor applications. Moreover, prior efforts relate to force sensing application of scanning probe microscopy as a result of strain in the transistor. Conversely, a BiMOS-embedded microcantilever detection invention is schematically illustrated in FIG. 37.

Figure 37A:
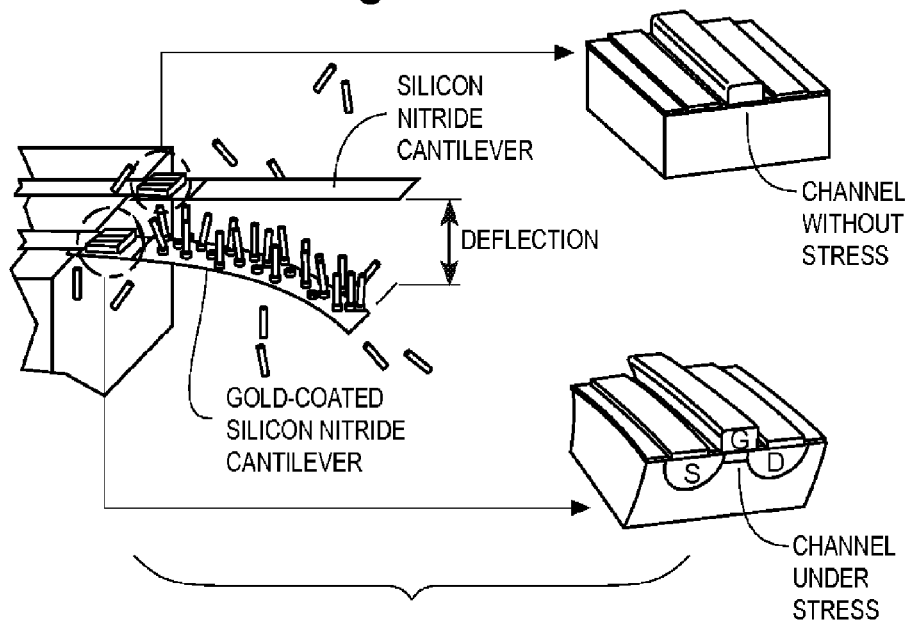
FIG. 37 illustrates a schematic of a BiMOS-embedded microcantilever detector.
Figure 37B:
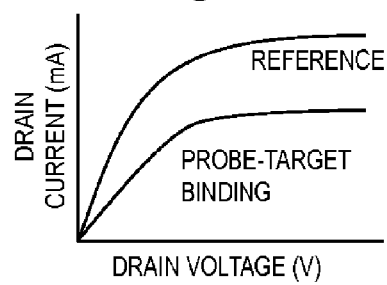
Figure 37C:
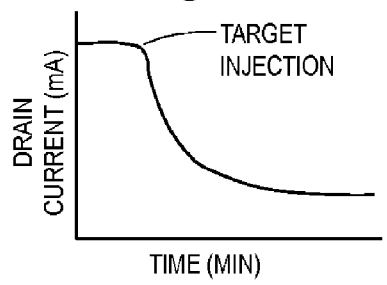

FIG. 37(A) illustrates a schematic of interaction between probe and target molecules on an embedded-MOSFET cantilever system. A silicon nitride cantilever is used as a reference and a gold-coated cantilever is used as a sensing cantilever. Specific biomolecular interactions between receptor and target or sensor bend the cantilever. A magnified view of embedded MOSFET in cross-section shows a stressed gate region when the cantilever bends, resulting in change of drain current due to conductivity modulation of the channel underneath the gate. FIG. 37(B) shows a schematic of change in a MOSFET drain current upon probe-target binding. FIG. 37(C) illustrates a change in drain current over a period of time due to deflection of a microcantilever.

Certain embodiments engineer an improved source-drain doping concentration, location at a high stress region (cantilever base), geometrical configuration (i.e., thickness and length of the cantilever), depth, channel doping and transistor W/L (width/length) ratio to improve sensitivity of an embedded BiMOS electronic detection paradigm. Certain embodiments reduce or minimize electronic noise by: (1) selecting localized doping regions on moderately resistive Si cantilevers (e.g., 10-15 $\Omega$-cm) to reduce unwanted noise due to carriers, (2) precise control of the doping region thickness (shallow source and drain junction depth, e.g., <0.5 μm), width and carriers to optimize the mobility, (3) sharper dopant step profile, and/or (4) large gate area design to suppress 1/f noise. In certain embodiments, MOSFET-embedded microcantilevers exhibit measurable, consistent and reproducible change in the drain current, even for deflection down to 1 nm. Thus, certain embodiments of embedded BiMOS detection systems provide a competitive level of optical detection for high-sensitivity analysis and surpass the reported piezoresistive and piezocapacitive based electronic detection methods.

In certain embodiments, microcantilevers can be fabricated from SOI (silicon-on-insulator) wafers with a 2.5 μm buried oxide etch-stop layer and a 1.5 μm epitaxial silicon layer. 50×1 cantilever arrays can be fabricated with the standard MEMS (micro-electro-mechanical systems) technology.

Embedded n-type MOSFET transistors can be fabricated on each individual microcantilever using standard CMOS fabrication, wherein the transistors are located at the rear part of the cantilever where surface stress is the highest. Once the MOSFET process is completed and tested for functionality, microcantilever shapes can be defined. Contact lithography can be done to make metal contacts to the gate, source and drain of individual microcantilevers. Finally, 2.5 μm oxide is etched to release the microcantilevers from the top. In certain embodiments, the transistor design process can be simplified with four masks and minimal process steps for ease of fabrication, thus making it a low cost fabrication of a high sensitivity electronic detection paradigm.

Figure 38A:
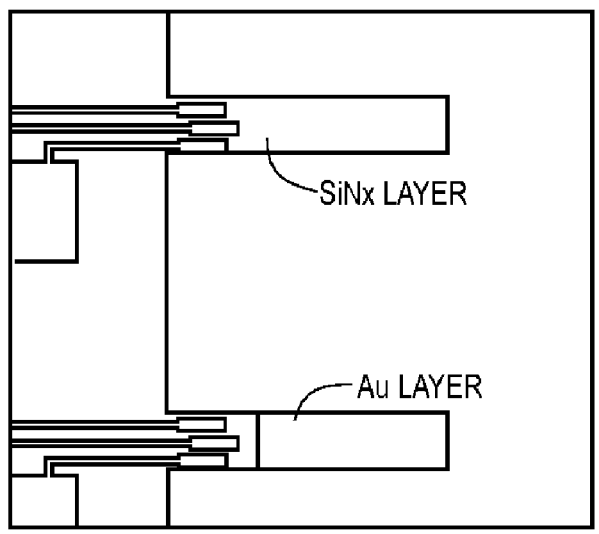
FIG. 38 illustrates exemplary scanning electron micrographs.

FIG. 38 illustrates exemplary scanning electron micrographs. FIG. 38(A) depicts a scanning electron micrograph showing an image of two identical or substantially similar cantilevers from a microcantilever array of 50×1 displaying an embedded MOSFET and geometry of a gold coated and $SiN_x$ cantilever beam approximately 250 μm long and 1.5 μm thick, with each leg approximately 50 µm wide. The pair of cantilevers includes one microcantilever coated with a thin film of Cr/Au (for immobilization of probe molecules, typically with thiol chemistry), which acts as a sensing microcantilever, while the other uncoated microcantilever is a reference microcantilever. A differential drain current between the sensing and the reference microcantilevers, which further reduces systematic noise and environmental perturbations, forms a basis for BiMOS electronic detection. A differential signal can be fed into a bipolar-based differential amplifier for electronic readout (BiMOS) at the chip level for future development, for example.

Figure 38B:
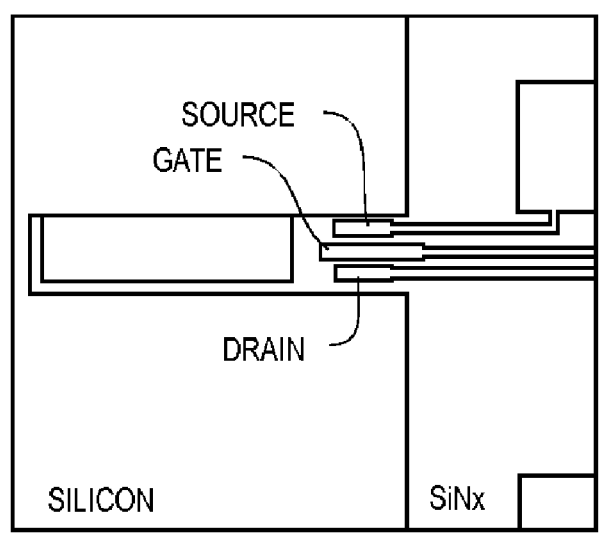

FIG. 38(B) displays details of MOSFET location on a cantilever beam. The beam is released by etching a 2.5 micron sacrificial oxide layer. FIG. 38(B) is a magnified view of a MOSFET-embedded sensing microcantilever. FIG. 38(B) highlights contact leads and physical separation of the Cr/Au layer and the contacts. Cantilevers with a thickness of 1.5-2 µm and length ranging from 200 to 300 µm are fabricated with a separation of about 250 µm between the reference and sensing microcantilevers for illustrative simplicity. The transistor is located about 2-4 µm from the cantilever base and the W/L ratio of source and drain is around 10 to achieve high transconductance, for example. The gate length can be kept to approximately 7-8 µm with 1 µm overlap with source and drain, for example. The resonance frequency of the MOSFET-embedded microcantilevers may be around 100-150 kHz, for example. Each array can be designed to have identical or substantially similar sensor (i.e., Cr/Au-coated) and $SiN_x$ reference microcantilevers for differential output to reduce systematic noise and possible false positives. An exemplary process layout for embedded BiMOS cantilevers is shown in FIG. 39.

As illustrated in FIG. 39, p-type silicon is first provided. Then, field oxide is provided around the silicon. An S/D window is opened in the field oxide over the silicon. P+ ions are then implanted in the S/D window. Next, a second mask of gate oxide is laid. Then, low stress nitride is deposited on the gate oxide layer, as shown in FIG. 39. After the nitride, a third cantilever mask is deposited, and the cantilever is etched. A fourth mask provides an open contact window. Lastly, a gold layer mask is provided, and the cantilever is released.

Figure 40A:
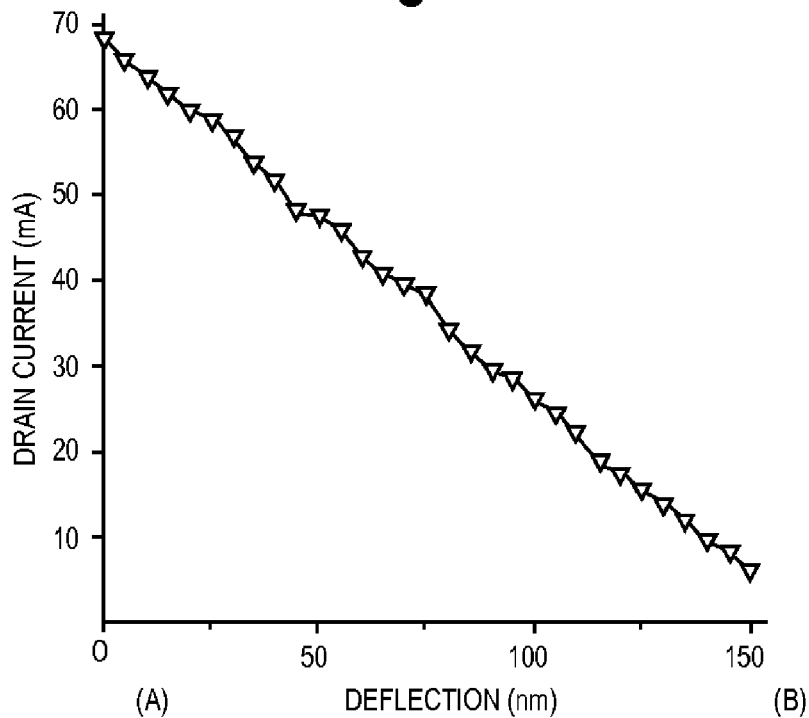
FIG. 40 shows a resultant change in drain current and noise measurement from a change in deflection.

In certain embodiments, high drain current sensitivity has been tested by physically bending a cantilever using a high resolution nanomanipulator which has less than 5 nm vertical resolution and which is integrated with a Cascade probe station and Keithley S4200 parametric analyzer, which can measure current down to femto-amps (fA). The cantilever was physically bent by the nanomanipulator in a downward direction and corresponding current-voltage characteristics were acquired at a fixed gate bias of 5 V. The microcantilever was bent down 150 nm with a step size of 5 nm, and FIG. 40(A) shows the resultant change in the drain current with physical bending. The plot was obtained by measuring the drain current at each cantilever bending (5 nm step) in the linear region of drain current-voltage characteristics. The decrease in drain current is between 0.1 to 0.2 mA per nanometer microcantilever deflection, thereby validating the high current sensitivity of MOSFET-embedded microcantilever to nanoscale deflection. As shown in FIG. 40(A), drain current changes by almost one order of magnitude between a few to 150 nanometers of microcantilever bending. The result demonstrates the high sensitivity of embedded BiMOS technology for detection of microcantilever bending. The bending results indicate that the MOSFET deflection sensitivity is of the same order as optical and almost two-to-three orders of magnitude higher than existing active and passive detection technologies.

Figure 40B:
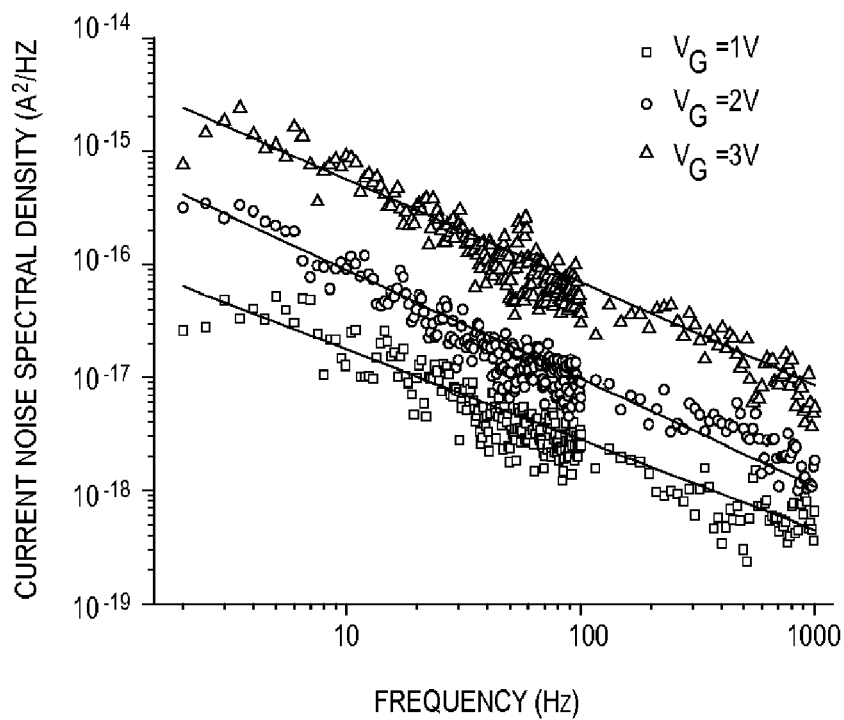

Moreover, MOSFETs have large signal-to-noise ratio owing to a large change in drain current and concomitant small noise density. This is evident from noise measurements shown in FIG. 40(B), whereas the three curves show 1/f noise for three different gate voltages. Flicker (1/f) noise is the dominant source of noise in MOSFETs at low frequencies, which influences device performance and the minimum detection limit of the sensor. To determine the low-frequency noise in drain current of an embedded MOSFET, current noise power spectral density was measured acquired. Measured spectra reveal current noise of approximately 20-40 nA, which is calculated by integrating the spectral power density over 1/f bandwidth for different gate voltages. Given that MOSFET current sensitivity is around 0.1-0.2 mA/nm of cantilever deflection, low detection limit can be readily achieved with large signal to noise ratio, thus further substantiating the high current sensitivity of a BiMOS detection paradigm. The noise density can be further reduced in subsequent generations of these devices by standard processing steps, involving optimization of doping concentration and reducing interface traps.

In certain embodiments, electronic measurements of the transistor characteristics were carried out using a Keithley 4200 semiconductor characterization system and a probe station. The observed changes in the drain current at gate bias and sweeping the drain voltage demonstrate the modulation of channel current with surface stress due to microcantilever bending. The large change in drain current results from the modulation of channel mobility because of surface stress, which increases the channel resistance. The mobility change may also arise from the changes in the interface charge densities, generation of trap-states, band structure alteration and generation of shallow defects due to localized bending stress.

Figure 41A:
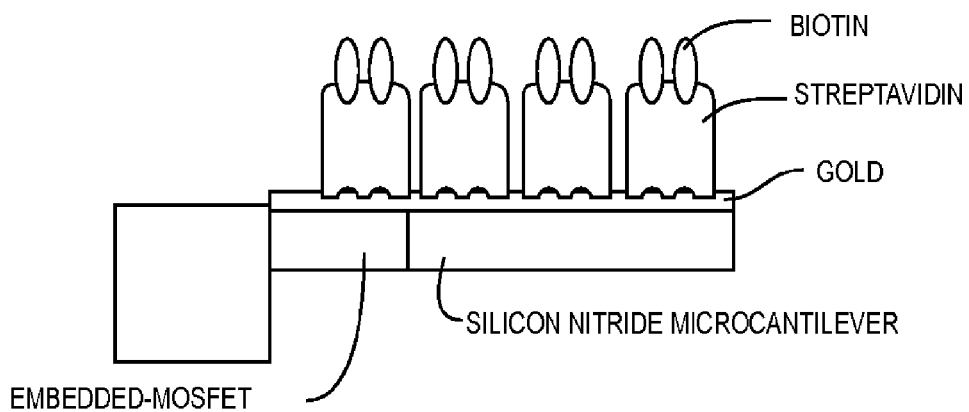
FIG. 41 illustrates an approach used to immobilize a probe and target in biomolecular binding experiments.

FIG. 41(A) illustrates an approach used to immobilize a probe and target in biomolecular binding experiments. The MOSFET-embedded microcantilevers were cleaned sequentially in acetone, isopropanol-2 and methanol for 10 minutes each, followed by UV-cleaning for 25 minutes, and were first functionalized with DTSSP ([3,3'-Dithiobis(sulfosuccinimidylpropionate)], Pierce Chemical Company), a linker molecule involved in immobilizing streptavidin to the gold-coated microcantilever surface. DTSSP was dissolved at 1.5 mM concentration in 5 mM sodium citrate buffer (pH=5.0), and the microcantilevers were immersed in the solution for 2 hours at room temperature to achieve strong adherence of DTSSP disulfide linkage to the gold coated surface (7). Streptavidin (Pierce) was subsequently immobilized on the microcantilever surface by incubating overnight in a 10 µg/ml streptavidin solution prepared with phosphate buffered saline (PBS, pH=7.4). This immobilization method provides a tight streptavidin layer with uniform density on gold for efficient binding of biotin. All the non-specific binding sites were blocked by bovine serum albumin (BSA) as a blocking agent. For detection experiments, the functionalized microcantilevers were exposed to 100 fg/ml, 100 pg/ml and 100 ng/ml of target biotin in PBS.

Figure 41B:
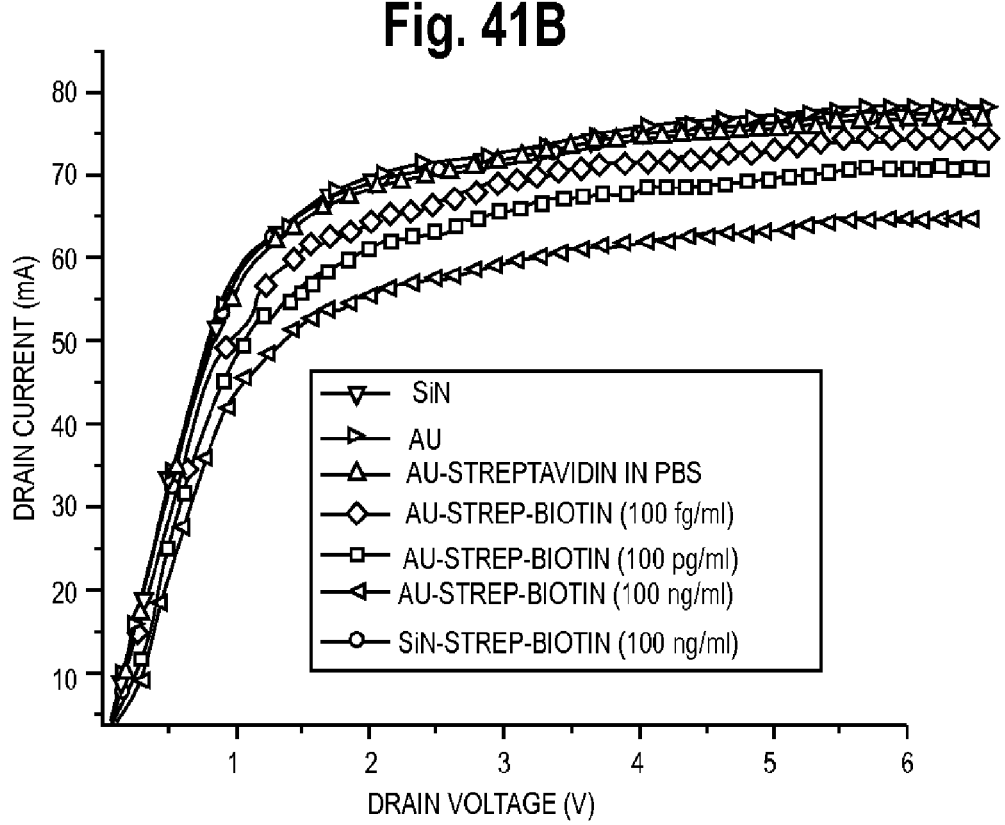

FIG. 41(A) illustrates a schematic side view of a $Si_3N_4$ cantilever coated with a thin gold layer showing immobilization scheme used in the experiments. FIG. 41(B) shows $I_D$ vs. $V_D$ characteristics of a gold-coated cantilever immobilized with streptavidin (10 µg/ml) immersed in phosphate-buffered saline (PBS). The experiment was carried out to check if presence of ions causes any significant bending of the cantilever beam. The experiment also shows almost negligible change in drain current on streptavidin (10 µg/ml) coated cantilever in absence of ligands (biotin). When biotin (100 fg/ml-100 ng/ml) is added, current decreases as the concentration increases which is indicative of cantilever bending. No drain current decrease was observed in silicon nitride reference cantilever indicating no probe-target binding In certain embodiments, MOSFET transistors were passivated with silicon nitride thin coating and electrical contacts were isolated for the binding measurements in the fluidic environment. A computer controlled ink-jet dispenser was used for dispensing fluid precisely on the cantilever surface. FIG. 41(B) shows the measured $I_D$ versus $V_{DS}$ characteristics for an n-MOSFET-embedded transistor, at $V_G$=5V. There is a negligible change in drain current when the streptavidin immobilized gold microcantilevers are immersed in PBS. The experiment was carried out to help ensure that the presence of ions in the solution is not causing any significant bending of the microcantilever beam. The MOSFET characteristics look similar to $Si_3N_4$ and gold coated cantilevers, which confirms minimal microcantilever deflection prior to specific binding of target molecules on cantilevers immersed in biotin solution. The plot also shows microcantilever bending as a result of streptavidin-biotin binding at very low concentration and current decreases further as concentration of biotin increases from 100 fg/ml to 100 ng/ml. The bending results from increase in compressive stress resulting from the repulsive electrostatic or steric intermolecular interactions, or by changes of the hydrophobicity of the surface. No drain current change was seen in $Si_3N_4$ cantilevers with biotin, where no binding events occurred. This result also underscores the high specificity of this preparatory method. These results demonstrate the high sensitivity of our method in detecting target molecules at very low concentration using all-electronic label-free detection approach.

Figure 42A:
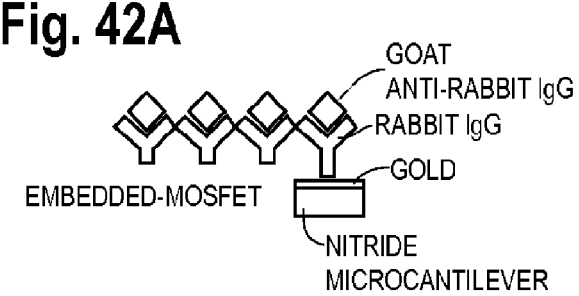
FIG. 42 shows rabbit $I_gG$ (primary antibody) and goat anti-rabbit $I_gG$ (secondary antibody) biomolecular binding detection with a MOSFET-embedded detection paradigm.

FIG. 42(A) shows a schematic illustration of a rabbit $I_gG$ (primary antibody) and goat anti-rabbit $I_gG$ (secondary antibody) biomolecular binding detection with a MOSFET-embedded detection paradigm. FIG. 42(A) shows a schematic side view of a $Si_3N_4$ cantilever coated with a thin gold layer showing immobilization scheme used in the experiments. After a cleaning procedure, the MOSFET-embedded microcantilevers are first functionalized with DTSSP as a linker and incubated overnight in 0.1 mg/ml rabbit anti-goat $I_gG$ (Pierce Chemical Company) prepared in PBS for immobilization. Bovine serum albumin (BSA) may also be used as an agent to block non-specific binding sites. Functionalized microcantilevers may be exposed to 0.1 mg/ml of goat anti-rabbit IgG in PBS for binding experiments.

Figure 42B:
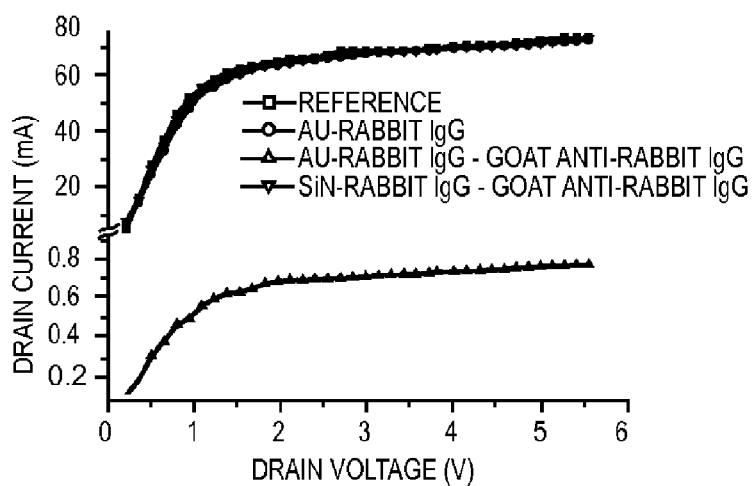
Figure 42C:
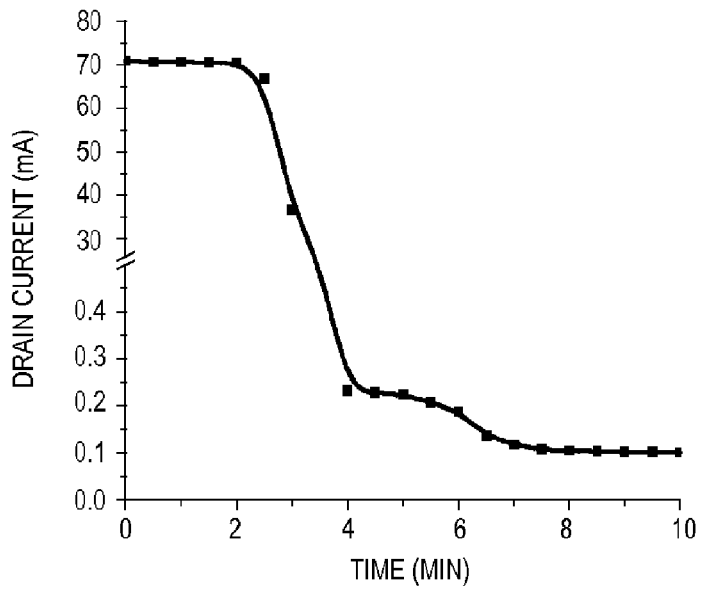

FIG. 42(B) shows measured $I_D$ versus $V_{DS}$ characteristics for an n-MOSFET transistor embedded in the microcantilevers, at $V_G$=5 V. There is no change in the drain current with $Si_3N_4$ and rabbit $I_gG$ coated cantilevers. When 0.1 mg/ml of goat anti-rabbit $I_gG$ was introduced, almost two orders of magnitude change in drain current was observed, which is indicative of microcantilever bending as a result of antibody-secondary antibody binding. Silicon nitride reference cantilever remained the same after injecting the target. FIG. 42(C) shows the rabbit $I_gG$ and goat anti-rabbit $I_gG$ interaction over a period of time at fixed drain voltage of 2 V. FIG. 42(C) demonstrates the large change in drain current with time, and then achieves the steady state saturation when molecular and surface interactions are completed.

The results at very low concentrations of molecules demonstrate high current sensitivity of certain embodiments, which are able to detect small cantilever deflections from specific bimolecular binding events, much below their threat level.

Validation of a BiMOS electronic detection system using physical bending and a representative example of biomolecular recognition with high sensitivity demonstrate a versatile method for detecting biological and chemical threat agents.

Moreover, the system is compatible with monolithic integration and potential for multiplexing signals on the same chip can reduce the wiring from outside and significantly reduce the device size and signal reader as well. BiMOS-embedded microcantilevers represent a significant paradigm shift in sensing technology, which can harness all the attractive attributes of emerging functional bio-nanostructures by integrating the label-free signal transduction and electronic detection directly on the highly successful complementary metal oxide semiconductor (CMOS) engineering platform.

Thus, certain embodiments provide an embedded BiMOS transistor for detection of cantilever bending due to biomolecular interaction. Deflection sensitivity is of the same order as optical detection. Deflection sensitivity is almost 3 orders of magnitude higher than existing passive and active (IGFET) electronic detection. Embedded BiMOS is capable of detection single molecular interaction, which is not possible with existing technologies.

Certain embodiments precisely place an embedded BiMOS transistor on high stress region of a cantilever. Certain embodiments provide fabrication of localized and ultra-shallow source and drain regions using optimal dopings at localized regions on a highly resistive cantilever. Localized piezo-resistive regions minimize or reduce thermal noise and corner frequency dramatically, which is a major source of low deflection noise in existing technologies. Certain embodiments allow measurement of current change without additional circuit directly due to cantilever bending rather than voltage as current change is almost insensitive to 1/f noise. Transistors are placed along the longitudinal direction of the cantilever where stress is greater and are used in a differential approach to measure current change as a result of cantilever bending.

Certain embodiments help eliminate Flicker Noise (1/f) as a major source of noise at low deflections. A MOSFET suffers from 1/f noise due to surface conduction. Certain embodiments eliminate the flicker noise by choosing localized doping regions on high resistive cantilevers to reduce unwanted noise due to carriers. Certain embodiments provide more precise control of the doping region thickness, width and carriers to optimize mobility. Dimensions of the transistor are configured to control 1/f noise. A large gate area is designed to suppress 1/f noise and low-noise applications. For example, certain embodiments minimize noise density to approx. 0.25 Å/√Hz.

In certain embodiments, a readout system is implemented on a chip. This hybrid design measures resistance, capacitance and current change on a single cantilever. Multiple readouts with different electronic detection paradigm can be made simultaneously, thus paving the way for complete system on chip based sensors for ultra-sensitive detection of bio-chemical threat agents.

Certain embodiments relate to developing system on a chip for smart sensors application, such as the hybrid sensor architecture system shown in FIG. 43. This system can perform three precision measurements on the cantilever:

1. Conductivity measurements: Finger electrodes on a cantilever chip can be used to measure conductivity changes when polymeric coating is exposed to various toxic gases/vapors. Toxic gases/vapors change an overall resistance of the finger electrodes and can be then detected.
2. Capacitance Measurements: An amount of surface charge that develops on the cantilever due to receptor-target interaction can be easily detected by this method on the microcantilever. This will quantify the surface coverage and the grafting density.

3. Cantilever bending due to embedded BiMOS technology (such as that described above).

Certain embodiments of hybrid sensor system arrays may determine a sensitivity of the system and also quantify surface coverage in one shot.

Additionally, certain embodiments provide thermal and infrared imaging with embedded MOSFET cantilevers. Thermal imaging based on detecting infrared (IR) radiation has revolutionized a variety of challenging tasks ranging from night vision to firefighting, medical diagnostics, and geophysical studies. IR detectors for thermal imaging can be classified broadly as either quantum or thermal detectors, with the latter group including pyroelectric and thermoresistive detectors.

Although quantum IR detectors—based on narrow-bandgap semiconductors—offer superior performance, they remain expensive and require cryogenic cooling. Due to the expense and cooling requirements, extensive effort has been made to develop thermal IR detectors in recent decades. Thermal IR detectors are essentially miniature calorimeters that measure the amount of heat produced in the detector upon absorption of IR radiation. The detectors can operate at, or even above, room temperatures. Despite successful commercialization of several detectors suitable for thermal imaging without cooling, there is still a need for a platform for thermal imagers that combines affordability, convenience of operation, and excellent performance.

Certain embodiments use a MOSFET drain current signal in a MOSFET-embedded micro cantilever-based focal plane array (FPA) to detect IR-induced deflection. Cantilevers can be coated with IR absorbing layers, for example.

Figure 44:
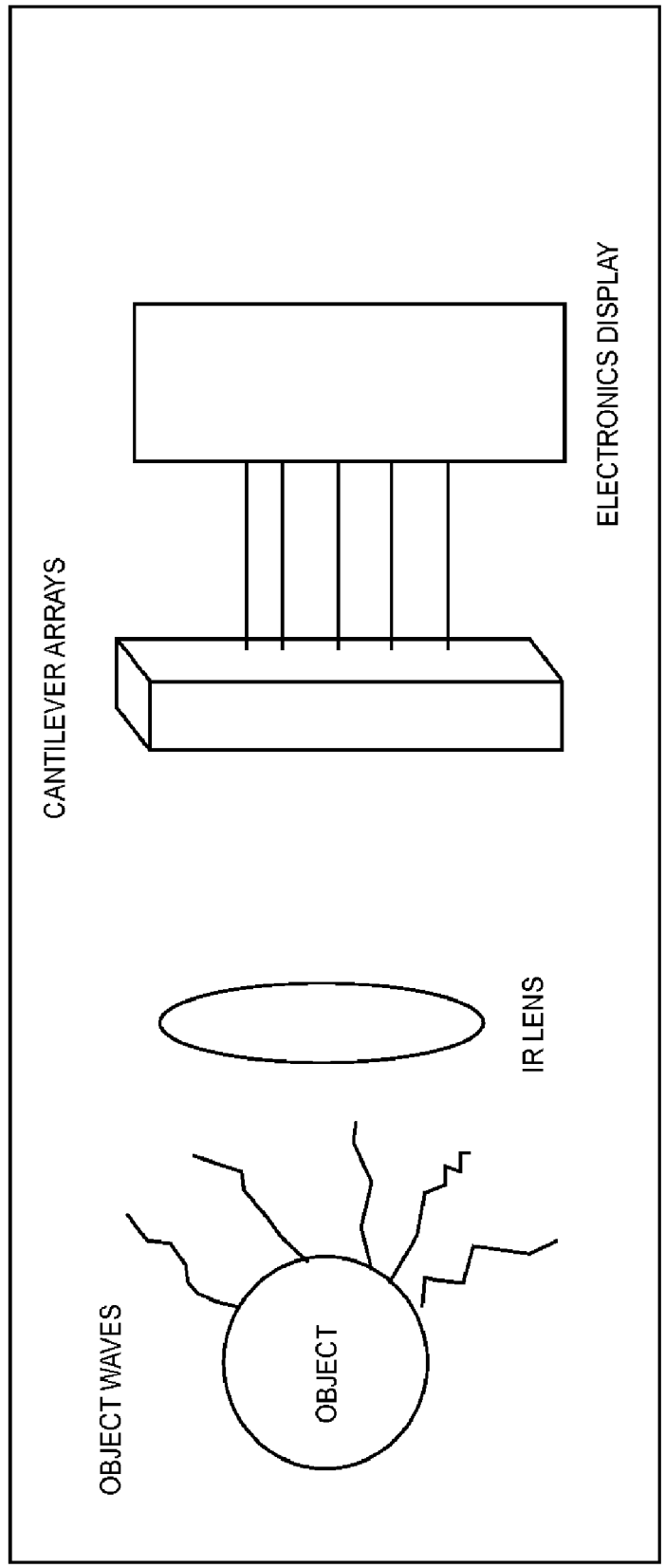
FIG. 44 shows an exemplary cantilever system.

An arrangement of such a system is shown in FIG. 44. The cantilever system includes an IR imaging lens and a microcantilever FPA with integrated electronic readout using embedded MOSFET cantilevers. The IR imaging system can measure the movement of each microcantilever and transform this information into a direct electronic image without further processing. The dynamic range, intrinsic noise, and resolution of the camera largely determine the performance of this system.

For example, certain embodiments can image objects with pixel size less than 10 micron, which has not been achieved by any other system to-date. Certain embodiments include closely spaced 2D cantilever assays each having individual on-chip electronic readouts using MOSFET embedded cantilever to achieve, for example, 10 micron pixel resolution. Cantilevers can be spaced approximately 5 µm apart, for example, and a width of the cantilever (which determines the pixel resolution) can be kept around 10-15 µm, for example. A Source and gate of the transistor may have a common terminal, and a drain of each transistor may be controlled separately. Such design allows design of a miniaturized handheld IR imaging system. Thermal coating can be carried out to attain a temperature sensitivity of approximately 0.1 mK, for example.

Many modifications and variations of the present invention are possible in light of the above teachings. Thus, it is to be understood that, within the scope of the appended claims, the invention may be practiced otherwise than as described hereinabove.

The invention claimed is:

1. A sensor for detecting mechanical perturbations represented by a change in an electrical signal, comprising:
   a structure; and
   a plurality of cascaded field effect transistors embedded in the structure, the cascaded field effect transistors having an associated electrical current that changes with mechanical perturbations in the structure,
   wherein the of cascaded field effect transistors are cascaded in series, and
   wherein the plurality of cascaded field effect transistors are BiMOS transistors.

2. A sensor for detecting mechanical perturbations represented by a change in an electrical signal as recited in claim 1 wherein the structure is a cantilever.

3. A sensor for detecting mechanical perturbations represented by a change in an electrical signal as recited in claim 1 wherein the sensor detects biomolecular interactions.

4. A sensor for detecting mechanical perturbations represented by a change in an electrical signal as recited in claim 1 wherein the plurality of cascaded field effect transistors are arranged across the length of the structure.

5. A sensor for detecting mechanical perturbations represented by a change in an electrical signal as recited in claim 1 further comprising readout electronics for measuring the electrical signal.

6. A sensor for detecting mechanical perturbations represented by a change in an electrical signal as recited in claim 5 wherein the readout electronics are passivated with an insulating layer for measuring the electrical signal in fluid.

7. A sensor for detecting mechanical perturbations represented by a change in an electrical signal as recited in claim 5 wherein the readout electronics are integrated with the plurality of cascaded field effect transistors.

8. A sensor for detecting mechanical perturbations represented by a change in an electrical signal as recited in claim 1 wherein each of the plurality of cascaded field effect transistors is capable of operation together or individually.

9. A sensor for detecting mechanical perturbations represented by a change in an electrical signal as recited in claim 1 wherein the structure is coated in gold.

10. A sensor for detecting mechanical perturbations represented by a change in an electrical signal as recited in claim 1 wherein the plurality of cascaded field effect transistors is configured for current flow perpendicular to the length of the structure or parallel to the length of the structure.

11. A sensor for detecting mechanical perturbations represented by a change in an electrical signal as recited in claim 1 wherein the plurality of cascaded field effect transistors is positioned on a high stress region of the structure.

12. A sensor for detecting mechanical perturbations represented by a change in an electrical signal as recited in claim 1 wherein the cascaded field effect transistors represent a plurality of embedded microcantilevers, and wherein the embedded microcantilevers include at least one reference microcantilever and at least one sense microcantilever.

13. A sensor for detecting mechanical perturbations represented by a change in an electrical signal, comprising:
   a structure; and
   a plurality of cascaded field effect transistors embedded in the structure, the cascaded field effect transistors having an associated electrical current that changes with mechanical perturbations in the structure,
   wherein the cascaded field effect transistors represent a plurality of embedded microcantilevers, and wherein the embedded microcantilevers include at least one reference microcantilever and at least one sense microcantilever.

14. A sensor for detecting mechanical perturbations represented by a change in an electrical signal as recited in claim 13, wherein the structure comprises a cantilever, and wherein the sensor is configured to detect biomolecular interactions.

15. A sensor for detecting mechanical perturbations represented by a change in an electrical signal as recited in claim 13, wherein the cascaded field effect transistors comprise at least one of the following: MOSFETs transistors and BiMOS transistors.

16. A sensor for detecting mechanical perturbations represented by a change in an electrical signal comprising:
a plurality of microcantilevers arranged to create an array of microcantilevers, the plurality of microcantilevers including at least one reference microcantilever and at least one sense microcantilever; and
a plurality of cascaded MOSFETs embedded in each of the plurality of microcantilevers, the MOSFETs having an associated electrical current that changes with mechanical perturbations in the microcantilever.

17. A sensor for detecting mechanical perturbations represented by a change in an electrical signal as recited in claim 16 wherein the at least one reference microcantilever comprises at least one $SiN_x$ microcantilever and the at least one sense microcantilever comprises at least one gold-coated microcantilever.

18. A sensor for detecting mechanical perturbations represented by a change in an electrical signal as recited in claim 16 wherein a carrier transport direction of the plurality of cascaded MOSFETs is perpendicular to the length of the microcantilever.

19. A sensor for detecting mechanical perturbations represented by a change in an electrical signal as recited in claim 16 wherein a carrier transport direction of the plurality of cascaded MOSFETs is parallel to the length of the microcantilever.

20. A sensor for detecting mechanical perturbations represented by a change in an electrical signal comprising:
a first microcantilever;
a second microcantilever;
a first series of cascaded MOSFETs embedded along a length of the first microcantilever, the first microcantilever having a surface coated with a material to which a probe molecule will adhere;
a second series of cascaded MOSFET embedded along a length of the second microcantilever; and
a differential amplifier coupled to the first and second series of cascaded MOSFETs to provide an electronic readout.

21. A sensor for detecting mechanical perturbations represented by a change in an electrical signal as recited in claim 20 wherein the MOSFETs in at least one of the first and second series of cascaded MOSFETs are capable of individual or coordinated operation.

22. A hybrid sensor system for performing conductivity measurement, capacitance measurement and cantilever bending measurement using a plurality of MOSFETs embedded on a cantilever, wherein said conductivity measurement is obtained by measuring a change in resistance of finger electrodes on said cantilever to detect a toxic gas or vapor, wherein said capacitance measurement is obtained by detecting an amount of surface charge on the cantilever due to receptor-target interaction and wherein said cantilever bending measurement is obtained using embedded BiMOS technology.

* * * * *

UNITED STATES PATENT AND TRADEMARK OFFICE
CERTIFICATE OF CORRECTION

PATENT NO. : 7,759,924 B2
APPLICATION NO. : 11/566557
DATED : July 20, 2010
INVENTOR(S) : Gajendra Shekhawat et al.

It is certified that error appears in the above-identified patent and that said Letters Patent is hereby corrected as shown below:

Column 1, lines 17-20, delete "This work was supported by the National Science Foundation (NSF) awards: #NSEC-EEC-0118025, and ECS-0330410, and Air Force Office of Scientific Research (AFOSR)-MURI #F49620-00-1-0283." and insert --This invention was made with government support under Grant Numbers EEC-0118025 and ECS-0330410 awarded by the National Science Foundation and Grant Number F49620-00-1-0283 awarded by the Air Force Office of Scientific Research. The government has certain rights in the invention.--

Signed and Sealed this

Nineteenth Day of October, 2010

David J. Kappos
*Director of the United States Patent and Trademark Office*